(12) United States Patent
Rogers

(10) Patent No.: US 9,855,178 B2
(45) Date of Patent: Jan. 2, 2018

(54) UNIVERSAL STERILE DRAPE AND SUPPORT SYSTEM FOR IN-OPERATING-ROOM SAFE PATIENT HANDLING EQUIPMENT

(71) Applicant: Kurk Anthony Rogers, San Diego, CA (US)

(72) Inventor: Kurk Anthony Rogers, San Diego, CA (US)

(73) Assignee: The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/688,099

(22) Filed: Apr. 16, 2015

(65) Prior Publication Data
US 2015/0231011 A1  Aug. 20, 2015

Related U.S. Application Data

(63) Continuation of application No. 13/593,456, filed on Aug. 23, 2012, now abandoned.

(60) Provisional application No. 61/526,993, filed on Aug. 24, 2011.

(51) Int. Cl.
 *A61B 19/08* (2006.01)
 *A61G 7/10* (2006.01)

(52) U.S. Cl.
 CPC .......... *A61G 7/1051* (2013.01); *A61B 19/081* (2013.01); *A61B 19/088* (2013.01); *A61G 7/1017* (2013.01); *A61G 7/1046* (2013.01)

(58) Field of Classification Search
 CPC .. A61G 7/1051; A61G 7/1046; A61G 7/1073; A61B 19/081; A61B 19/088; A61B 17/0293; A61B 2019/085; A61B 19/08; A61B 19/10; A61B 2019/106; B66C 1/00; A61F 5/37
 See application file for complete search history.

*Primary Examiner* — Ophelia A Hawthorne
(74) *Attorney, Agent, or Firm* — Erickson Kernell IP, LLC

(57) ABSTRACT

Described are surgical drapes and system with universal application to heavy equipment useful in operating room environments. Surgical drape systems of the invention are particularly capable of covering patient support machinery such as hoists, lifts, and slings, whether the equipment is mobile or stationary, or configured as a floor-based or as an overhead support/lifting system. The drapes of the current invention provide for protecting the equipment from exposure to surgical biohazard waste e.g.; blood or body fluids, as well as providing the ability to use equipment that is otherwise not presently allowed to enter into an operating room because of the impossibility to render such equipment sterile. The drapes further allow for the holding, lifting and positioning of the patient whole body or limbs while maintaining sterility during prepping and surgical procedures. Also included are support slings for use with the drapes.

4 Claims, 27 Drawing Sheets

UNIVERSAL STERILE DRAPE AND SUPPORT SYSTEM FOR IN-OPERATING-ROOM SAFE PATIENT HANDLING EQUIPMENT

CROSS REFERENCE TO RELATED APPLICATIONS

This application is a continuation of application Ser. No. 13/593,456, filed Aug. 23, 2012, now abandoned, which claims the benefit of provisional application Ser. No. 61/526,993, filed Aug. 24, 2011.

FIELD OF THE INVENTION

This invention relates to safe patient handling and care during surgical procedures under sterile conditions. More particularly, this invention relates to universal drape designs, slings, and lifting crossbars for heavy equipment presently not used in operating room environments due to their bulky and very large surface area designs which make cleaning to sterile conditions futile. Even more particularly, this invention relates to polyethylene and polypropylene sterile drapes and drape configurations for covering large patient handling machinery for use in the operative environment that is particularly difficult to clean or otherwise maintain in a sterile condition, such as patient hoists and lifting motors, frames, yokes and crossbars.

BACKGROUND OF THE INVENTION

The following description in this Background section includes information that may be useful in understanding the present invention. It is not an admission that any such information is prior art, or relevant, to the presently claimed inventions, or that any publication specifically or implicitly referenced is prior art.

Safe patient handling, care and maintenance have been the penultimate focus in hospital and operating room environments for decades. In such focus the desire to maintain a truly sterile environment during surgical procedures in the operating room has led to a long lasting paradigm of directing attention for sterility to that of the patient him/herself. Thus, prior systems for creating sterility have related to using sterile drapes for covering the patient, in whole or in part, leaving only the body area to be treated exposed to the surgeon's hands and utensils.

The prior art is replete with patient draping systems. For example, U.S. Pat. No. 4,119,093 to Goodman discloses a drape system for covering a patient's limb while also covering adjoining patient torso and surrounding area. U.S. Pat. No. 3,930,497 to Krebs et al discloses a patient body drape that allows exposure of limbs. U.S. Pat. No. 6,725,864 to Ewonce et al discloses a patient drape for covering the patient's shoulder. In another example, U.S. Pat. No. 4,169,472 to Morris discloses a patient drape that also includes fluid collecting capability. U.S. Pat. No. 4,945,924 and U.S. Pat. RE35,427 to Poettgen disclose patient drapes that have an insulation quality. U.S. Pat. No. 4,334,529 to Wirth discloses a patient drape equipped with holes for channeling cables from a nonsterile equipment side to a sterile surgery side. In U.S. Pat. No. 5,010,899 to Thompson, a patient drape is disclosed that includes loops for directing surgical equipment, such as tubes and wires. U.S. Pat. Nos. 6,055,987 and 6,216,700 to Griesbach disclose a patient drape with hook and loop type fasteners. In U.S. Pat. Nos. 5,341,821, and 5,454,381 to DeHart, a patient drape is disclosed wherein the drape has transparent sections to assist the surgeon viewing while in U.S. Pat. No. 6,612,310 to Sklar a patient drape is disclosed with a window for viewing non-sterile equipment such as monitors close to the actual surgical site. Other drape systems have sought to cover the patient in a canopy such as disclosed in U.S. Pat. No. 6,367,476 to Conn but such a system is still patient drape based.

While sterile patient drapes as noted above have proven useful in their myriad forms, they predominantly focus on draping the patient and surrounding adjacent areas of the operating theater, as opposed to surgical equipment alone for the sake of creating a sterile environment about the equipment. Thus, there is a need for inventions to address creating a sterile environment about non-sterile operating room equipment.

Some drape systems have sought to cover a limited type of operating room fixtures such as the operating table itself as disclosed in U.S. Pat. No. 5,875,780 to Rodriguez, U.S. Pat. No. 4,164,941 to Knapick et al and U.S. Pat. No. 7,604,007 to Wooley, but operating tables comprise fixtures that are indelibly tied to a surgical area of operation providing sterile working space for the doctors to place surgical equipment close to their proximity.

With the increasing advent of hospital or care facility born infections, commonly referred to as "hospital associated infections" or HAis, there has been an increased awareness for the need for sterilizing equipment within an operating room. It is well known that operating rooms and other areas in hospitals should be sterile in order to prevent hospital acquired infections. Despite this knowledge, hospital acquired infections are a significant problem in the healthcare system. It has been estimated that 5% of all hospitalizations in the U.S. are associated with a hospital-acquired infection. Additionally, the CDC in 2009 estimated that the direct cost of hospital associated infections for U.S. hospitals was in the range of $29-$45 billion dollars. The current procedure for sterilization of powered equipment, according to the Association of Perioperative Registered Nurses mainly involves, among other things, wiping down the equipment with manufacturer-recommended detergent/germicide and then drying the equipment with a lint free cloth. Common methods of sterilization used in hospitals for cleansing non-electronic instruments include sterilization with steam/autoclave systems, chemicals such as bleach and peroxide, dry heat, and ethylene oxide gas. Radiation methods such as gamma ray exposure, electron beam processing, X-rays, and ultraviolet rays can also be used to sterilize medical equipment.

Although manual sterilization techniques for heavy equipment as noted above are available, their application is highly problematic and time consuming. In some sterilization methods, the equipment would have to be taken to a special area for such as electron beam or gamma ray exposure, or the beam and ray sources would have to be transported to the operating room. The same would be true for ethylene oxide gas, X-rays and UV radiation wherein the entire operating room containing the equipment would have to be exposed. Given the impracticality of constantly re-sterilizing operating room equipment manually before each surgery, a solution is recognized to use sterile draping for equipment. For example, clear and opaque drapes have been designed to covering a C-Arm fluoroscopes which are used in surgery. Other drapes include clear plastic for covering X-ray cassettes and X-ray intensifiers, microscopes, and hand held electronic modules for controlling large equipment. There are also drapes for such as a cart for supporting a C-arm imaging system, a drape for a medical cart, see U.S. Pat. No. 6,497,233 to DeAngelis, which is merely a rectangular sheet, a drape for a pivoting arm for supporting a limb such as disclosed in pivot arm U.S. Pat. No. 6,629,944 to Smart, and systems for securing drapes to medical equipment such as U.S. Pat. No. 7,775,213 to Henke-Sarmento et al, and large dimensioned general purpose drapes for covering OR equipment such as U.S. Patent application 2006/0150987 to Dillon et al.

Although the above equipment draping concepts have been disclosed, none of them apply to the specific concerns regarding patient handling equipment such as patient hoists, lifts and the like. Rather, much of the equipment drape systems merely comprise sheets of material that can be used to wrap around operating room equipment but cannot easily accommodate support structures built into patient lifting devices.

Concerning safe patient handling issues as it relates to sterility and the sterile environment of the operating room, often times there is a need to manipulate and position a patient while in the operating room before surgery, during surgery, and/or after surgery, all under sterile conditions. Patients are hung in a gurney or otherwise in a sling, for example, a limb is propped up or supported in a sling by a hoist, and the patient positioned for surgery and draped. If the patient's body or limb must be repositioned, the sterile draping is disturbed by the need to manipulate the patient against the non-sterile sling. Further, presently doctors and operating room staff must themselves physically lift, hold, and rotate patients and/or patient body parts, such as arms and legs, all of which weigh substantial poundage. Such patient body manipulation is often problematic in numerous ways with respect to safe patient handling including danger to patient from accidentally being dropped, and subsequent loss of sterile environment due to a patient drape, or part thereof, touching non-sterile and non-prepped slings or other operating room equipment. Under such conditions, not only is the patient at risk of mishandling, the operating room staff is also at risk in the form of body injury from lifting and supporting patient body and body part weight and often at angles unfit for maintenance of good back muscle health. Thus, a focus on draping the patient as opposed to draping operating room patient handling equipment has set up work environment conditions that can result in occupational injuries to hospital operating room staff.

For example, according to the Bureau of Labor and Statistics, nurses' aides, orderlies, and attendants had 44,930 days away from work due to injury in 2007. Their injury rate was 465 cases per 10,000 workers. These figures are higher than for construction workers who had 34,180 days away from work and an injury rate of 394 cases per 10,000 workers. Further, the musculoskeletal disorder rate of the healthcare workers cited above (252 casesper 10,000 workers) was more than seven times the average national rate for all occupations. (American Nurse Today; July 2010, Vol. 5. No. 7, Patient handling: Fact vs. Fiction, Ninica L. Howard M S, CPE.) Other studies have shown that institution of safe patient handling techniques which comprise use of lifting devices not only saved institutions large sums of money, they have actually recaptured the costs of using such equipment by the savings on workers compensation for injuries caused by lifting patients by hand. (Spiegel, Jerry, Analee Yassi, Lisa Ronald, Robert Tate, Penny Hacking, Teresa Colby, "Implementing a resident lifting system in an extended care hospital: Demonstrating Cost-Benefit," *AAOHN Journal*, March 2002, 50(3). Nelson, Audrey, Mary Matz, Fangfei Chen, Kris Siddharthan, John Lloyd, Guy Fragala, "Development and evaluation of a multifaceted ergonomics program to prevent injuries associated with patient handling tasks," *International Journal of Nursing Studies*, August 2006, 43(6). Collins, J. W., L. Wolf, J. Bell, B. Evanoff "An evaluation of a'best practices' musculoskeletal injury prevention program in nursing homes," *Injury Prevention,* 2004, 10. National Institute for Occupational Safety and Health (NIOSH), Centers for Disease Control and Prevention, Department of Health and Human Services, *Safe Lifting and Movement of Nursing Home Residents*, February 2006.) Thus, there is a need to create inventions that will lower the number of healthcare worker injuries caused by heavy lifting and to provide for placement of otherwise unsterilizable equipment in the operating room under sterile conditions.

Surgical slings for lifting or supporting a patient are similar to the surgical drape in that prior sling devices were not typically made sterile in and of themselves. Rather, sterile drape material was used between the lifting/support sling and the patient if a lifting device is used at all. U.S. Pat. Nos. 4,702,465 and 4,848,363 to McConnell, for example, discloses a telescoping sterile upright support assembly wherein a lifting/support apparatus is not sterilized and not draped but nonetheless described for use within the sterile field in the operating room. The apparatus is designed to hang into the sterile field thus allowing its easy entry and exit from the surgery area. Thus, certain devices for lifting patient body parts have been disclosed for uses within a sterile environment, but there is no conception disclosed for a sterile patient body support sling and/or hoist system designed for use in patient handling within the sterile environment. Moreover, the present hoisting system components such as crossbars to which slings are attached are lacking in design in that due to sling hanging points manufactured at the ends of the bar, and the methodology and need to attach sling loops at those limited locations, causes the sling to bunch up and in turn cause undesired pressure and compression on patient body parts.

As will be disclosed below, notwithstanding the numerous prior surgical drape configurations, there remains a long felt need in the art of safe patient handling, particularly in sterile operating room environments, for drape systems, slings and improved lifting device components such as crossbars that will provide the ability to use, within the operating room and under sterile conditions, bulky equipment and machinery, such as patient body lifting and support cranes, jacks, and hoists and the like, and the lifting slings and crossbars that function with the lifting devices.

SUMMARY OF THE INVENTION

Definitions

Before describing the instant invention in detail, several terms used in the context of the present invention will be defined. In addition to these terms, others are defined elsewhere in the specification as necessary. Unless otherwise expressly defined herein, terms of art used in this specification will have their art-recognized meanings.

Other features and advantages of the invention will be apparent from the following drawings, detailed description, and appended claims.

"Polyethylene" drape or PE drape as used herein refers generally to sheet material made out of PE that is commonly used in the manufacture of sterile hospital garments and drapes. The manufacturing process comprises making non-woven fabric from spunbond olefin fibers by RF, heat, and pressure technologies. Generally, the material is a two to eight layered fabric. In a preferred embodiment, the fabric can be shaped as it is fabricated from low density polythene (LDPE). As a PE drape is referred to in this disclosure, the multiple layers can be latex free and comprise PE, paper tissue, and siliconized paper tissue. References to PE herein are also considered to include Polypropylene based material that can be used in conjunction with polyethylene. Additionally, PE can be opaque or transparent. Also, separate pieces of PE can be sealed together using radio frequency technology.

"Patient drape" refers to generally sterile drapes used to cover patients and patient body parts in preparation for surgical procedures in sterile operating room environments. Such drapes are distinct from drapes for equipment.

"Operating room equipment drape" refers generally to surgical drapes for covering hard equipment used in the operating room and particularly the operating theater. Operating room equipment drapes are the drape that is the subject of the current invention and can comprise any nature of material suitable for being made sterile and for use in covering electronic device racks and stands, mobile drip bag stands, tables and body support structures, such as floor based mobile patient hoists and hoist systems, overhead and ceiling mounted patient hoists, and the like. In preferred embodiments the drape material can comprise a single layer material or any number of layers of material. In other preferred embodiments the material can be either opaque or clear. In still further preferred embodiments the drape material can comprise PE (i.e., polyethylene or in the alternate polypropylene based material).

"Sealed sling" refers to a patient body or body part support sling that is covered in PE draping. A sealed sling also refers to slings covered in PE further containing reinforced PE webbing. A sealed sling of the invention can be made sterile to ISO 14644 Class B standards using well known Ethylene oxide and gamma radiation techniques.

Turning now to the invention, in a first embodiment, the invention comprises sterile drapes comprising designs and systems for draping heavy operating room capable equipment. In a related embodiment, the equipment for which the draping materials and systems are designed to cover include, for example, patient lifting and support hoists, hoist motors, hoist straps, hoist framing and structures and the like, yokes and crossbars or sling support bars, for both stationary and mobile as well as floor-based or overhead or ceiling fixed equipment. In further related embodiments, the invention drape can be material that is loose fitting or closely fitted to patient lifting device structures.

In a second embodiment, the invention further comprises sterile patient support slings for use in supporting patient body and body parts during surgical procedures under sterile conditions. In a preferred embodiment, the slings work in concert with the sterile drape covering the equipment, such as a motor driven hoist. The slings of the invention further comprise important features that improve the usefulness of slings in a surgical environment including slots for insertion of belts for securing a patient and side pockets for keeping unused sling loops and sling material secure and out of the way while remaining in a sterile condition.

In a third embodiment, the invention further comprises novel and improved crossbars for hanging slings containing multiple sling loops and for improving the positioning of slings in general.

In a fourth embodiment, draping materials and system comprise any suitable fabric for use in the operating room arena, particularly the operating theater. In a particularly preferred embodiment the drape material is amenable to sterilization processes appropriate for use in surgery. Thus, the invention operating room equipment drape contemplates use of any material whether now commonly applied to sterile drape use or not. In one preferred embodiment, said draped can comprise PE based fabric commonly used for sterile environments. Preferably, the fabric is constructed in either a pleated or accordion fold style such that the fabric can be neatly collapsed or expanded similar to an accordion, or alternatively the fabric can be unfolded or non-pleated. Further, the fabric can be opaque or clear. In a related embodiment the fabric, whether non-pleated (i.e., plain fabric) or pleated (i.e., accordion folded) styles, the sheet of fabric making up the plain or accordion styled form can be wrapped in a circle such that the opposite ends of the sheet are adjoining and fixed together. On accordion-style drape sheets, by way of description but not to limit the scope of the invention, the opposite ends to be adjoined for fixing together are those that when the ends are affixed, the drape will form a tube and the accordion folds will allow expansion of the drape from a folded position to expand along the length of the tube formed by joining said ends. For plain configurations, the drape material can be formed into a tube and sterilized in a bunched or alternatively telescoped format to assist in sliding it over equipment as it is expanded. Similarly, accordion-configured tubes are sterilized in a folded format so that the drape can be slid over the operating room machine as the accordion pleats unfold. In a further related embodiment, one end of the tubular formed (plain or accordion) drape is constructed of clear polyethylene. The clear polyethylene allows the technician to see the yoke and cross bar as the drape is slid over the hoist support structure. The clear material will further assist the operating room personnel to see the specifics of the hooks on the crossbar. In still further related embodiments, the clear section of the tube is closed and can be sized to fit with greater specificity than just a bag shape. Specifically, the clear section can be formed to allow insertion of a crossbar such that there is a closer tolerance fit of the crossbar within the bag. In still a further embodiment the sections of the clear area that contact or will be within the contact area of the crossbar's hook and clasp, typically a carabineer style clasp, is further covered in a reinforced PE webbing which provides for protection against stressing or tearing of the PE drape material at such high strain areas.

In a fifth embodiment, the invention draping materials further contemplate both specific and universal dimensions in the sizing of the tubular formed drapes, whether of plain or accordion style. In a preferred embodiment, the sizing of the drape tube diameters is generally dimensioned for use with both floor-based and overhead or ceiling-based patient lifting hoists and their support bar attachments. The drapes for both the floor-based and overhead hoists can be shaped to fit the profile of the specific configuration, e.g., floor or overhead model in plain or accordion configuration.

In a sixth embodiment, the invention contemplates attachment to the drape material, whether plain or accordion tubes, periodic or spaced polyethylene tabs of varying lengths but generally between three inches and 24 inches in length, more commonly between six and 18 inches, and comprising polyethylene and containing an acrylic self-adhesive tab at the terminal portion thereof, such as for example, in tape, or glue, and the like protected by a disposable cover. In a particularly preferred embodiment, the tabs are useful for wrapping around and gathering up excess drape material, or otherwise aiding in the securing of the drape on the equipment, particularly of plain or accordion style drape in tube form, and maintaining the bunched excess drape material in position by removal of the covering of the adhesive and contacting the sticky portion of the tab back to the drape. Additionally, the tabs can be specifically placed on the drape at locations to perform specific functions, such as securing excess drape at predetermined positions. In a further related embodiment, the tubular drapes include an elastic or otherwise expandable band woven in or otherwise fixed at the opening edge of the drape allowing for the automatic securing or tightening up of the drape opening around the operating room equipment. Typically, the elastic band has a range of stretch or expansion to accommodate positioning of the drape around obstacles making up the equipment.

In a seventh embodiment, the invention comprises polyethylene-sealed sterile sling assemblies further comprising, similarly to the clear drape portion covering the crossbar hook, a polyethylene webbing, made of woven PE, or blends of polypropylene or polyethylene, for reinforcing the hanging loops used to hang the slings. In a particularly preferred embodiment, PE reinforcement covers the sling, sling loops and across the bed of the sling. The slings, sealed as they are in PE, are of generic and various lengths and sizes and intended for use in sterile environments with the operating room equipment, for example, a patient lifting hoist covered in the drape systems of the present invention. In a related embodiment, the woven polyethylene webbing material can be incorporated by fusing, gluing, stitching, RF and the like, to the clear polyethylene covering at the area inside of the sling loops and inside of the yoke assembly of the typical hoist to provide strength and prevent tearing during patient handling with the sling. Further embodiments include belt slots and at least one and preferably two sterility pockets running the length of the sling as detailed below.

In an eighth embodiment, the invention drape system comprises new and improved hoist cross bars that provide variability in the hanging position of sling loops. In a preferred embodiment, the crossbars have multiple hanging positions manufactured into the bar at generic positions according to generic measurements incorporated into typical sling designs. In a particularly preferred embodiment, the crossbar of the invention has not only sling hooks at its terminal portion, it also has at least four and as many as six additional internal loop receptacles for hanging loops that are spaced along the upper length of the cross bar. In a further preferred embodiment, the internal loops can be individually positioned along the bar and are lockable so that they can be set at one position or adjusted in position as desired.

Additional embodiments of the invention comprises sterile drape systems and methods for covering floor-based patient lifting devices that include belts and/or booms attached to yokes, drape systems for covering overhead lift assemblies including their motors, yoke and boom assemblies, and drape systems incorporating disposable sterile sling assemblies of generic and various designs and sized dimensions to lift and hold patient bodies and limbs. In related embodiments disposable sterile slings with sling loops are covered with polyethylene and include drape material forming loops generally located at the end portions of the slings for attachment to booms or yoke of the lifting device. In a particularly preferred embodiment the loops are formed of reinforced/woven polyethylene drape material incorporated and/or fused into the polyethylene drape for strength and prevention of tearing at the contact point between sealed sling loop and sling drape material covering the hook area of the crossbar. For large slings, the reinforced loops can be located at any position around the outer edge of the sling. For example, a sling for holding a prone human body can have sling loops spaced along opposite edges of the sling fabric. In a particularly preferred embodiment, the sling loops can comprise two attachment points for hanging to a cross bar of a patient lifting device and for adjusting positioning of body parts such as arms and legs.

Further still, other embodiments of the invention comprise disposable sterile sling assemblies of various lengths and sizes for use in repositioning patients' limbs or head under sterile conditions, such as on an operating table or a clinical exam table. Such sling assemblies for repositioning a patient appendage are distinguishable from patient body lifting and holding slings in that the repositioning slings are generally smaller than slings for lifting and holding whole patient body weight and have two sling loop attachment points each of which can be single or double hanging positions for uses of adjusting position as stated above.

BRIEF DESCRIPTION OF THE DRAWINGS

FIGS. 2A and 2B are shown with an elastic band 17.

In FIG. 6A an accordion styled drape design that comprises a tapered tube drape becoming narrower at the closed crossbar end than at the opened end.

In FIG. 8A, clear portion 13 covers crossbar B with PE reinforcement webbing 25 nestled in the hook portion of the crossbar. FIG. 8B is a close-up of one side of the clear portion 13 with the reinforcement strapping 35 in the area that will saddle in the hook cradle of the crossbar. In FIGS. 8C and D are shown two depictions wherein the PE reinforcement webbing 25 is applied to the areas of the drape clear fabric that will contact the crossbar hook. In FIG. 8C the bag of the clear drape is folded in the shape to match the crossbar and in FIG. 8D the clear section is shown in an unfolded state prior to forming around the crossbar and hook. In FIG. 8E is depicted a close-up drawing of one side of a crossbar 70 with its hook 72 and retaining clasp 71. In FIG. 8F the drape clear section 13 is shown covering the bar and its hook section while FIG. 8G shows the drape as it will contact with the reinforced sling loop 75. As depicted, reinforcement webbing is formed into the drape material and covers the loop.

In FIG. 9A, a full body support sling 30 with reinforced loops 19 sealed in PE 21. In FIG. 9A the sling 30 is shown in its hanging position and with reinforced PE webbing 20 along the outer edges of the sling and covering the loops 19. The full body sling possesses slots 32 for insertion there through of a security belt that can be rubber, nylon or muslin, for example, such as an adjustable belt with end clasps. FIG. 9B shows additional detail. The loops 19 comprise reinforced PE by webbing 20 which is formed over the loops and hang points 22 of the loop. The loops comprise two loops each 23 and 24 that provide separate hanging points. The bed of the sling includes a plurality of belt slots 32 and reinforcing webbing across the body of the sling. In FIG. 9C is depicted a patient tie down strap hermetically sealed in PE and PE webbing.

In FIG. 10A, is shown a partial cross section of the area noted in FIG. 9B from a×b showing a perspective drawing (direction 'a' is oriented into out of the drawing page) wherein sling material 30 is covered or otherwise sealed within sterile PE drape material 31 and reinforced with webbing 20 along the sling edge which also covers or otherwise form the loops 23 and 24. In FIG. 10B is depicted one embodiment of the sling loop hanging from the covered crossbar. Reinforcement sections 25 of the drape contact the loop.

In FIG. 11A, the internal hooks are manufactured in a fixed position to accommodate standard sling measurements. There are sling hooks on the terminal ends 91 and at least two, preferably three and even more preferably four additional sling hooks 92, 93, 94, and 95 on either side of the hanging belt.

In FIG. 12A, the crossbar 90 (which is typically hollow high tensile strength steel, aluminum or composite square tube) is shown comprising a slot 96 and adjustment holes 97.

DETAILED DESCRIPTION OF THE PREFERRED EMBODIMENTS

Figure 1A:
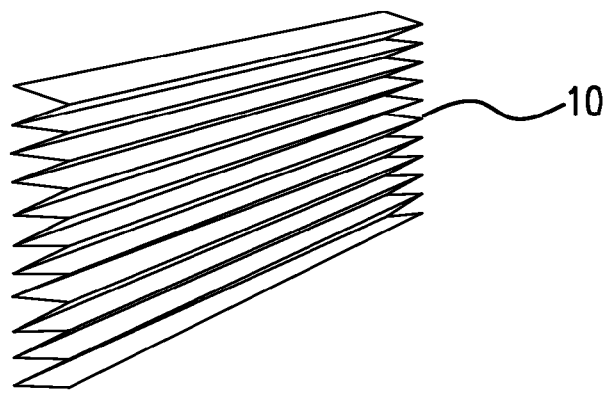
FIGS. 1A, B, C and D are drawings showing pleated or accordion styled drape material 10. In 1A the accordion drape material is planar. In 1B the accordion drape material 10A is shown formed circular, and in 1C the drape is formed in an accordion tube 10B with incorporated elastic band 17 and handling pouches 16 located at the open end of the drape.
Figure 1B:
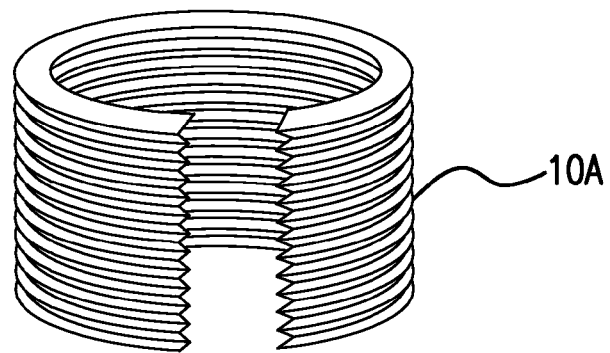
In FIG. 1D is shown a completed drape example of one embodiment of the invention wherein the drape comprises a tubular accordion-folded main body 10C with open end 11, elastic band incorporated therein 17, tabs 14 with adhesive 15 at tab 14 ends, and a section of clear PE, 13, forming the end of the drape which is closed at the end 12. Opposing sides of the clear portion 13 have incorporated PE reinforcement webbing 25. The drape is shown to have diameter dimension 'a' and length b'. (Handling pockets not shown in FIG. 1D.)
Figure 1C:
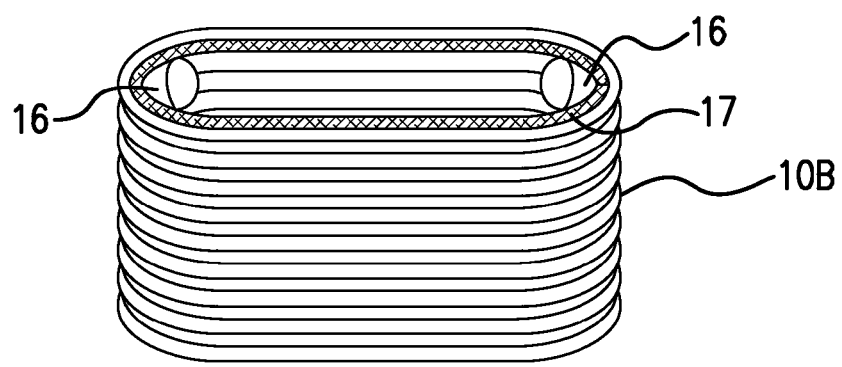

As those in the art will appreciate, the following description describes certain preferred embodiments of the invention in detail, and is thus only representative and does not depict the actual scope of the invention. Before describing the present invention in detail, it is understood that the invention is not limited to the particular device arrangements, systems, and methodologies described, as these may vary. It is also to be understood that the terminology used herein is for the purpose of describing particular embodiments only, and is not intended to limit the scope of the invention defined by the appended claims.

In a first embodiment, the invention comprises sterile draping materials, designs and systems for draping heavy operating room capable equipment. As those in the art will appreciate, such drapes will preferably be used once and then be appropriately discarded. As such, the drapes are considered to be single use, disposable items, although under certain circumstances they may be cleaned and/or re-used, provided they are made of suitable materials and the applicable procedures allow for more than one use and/or cleaning between uses. The equipment for which the draping materials and systems are designed to cover include, for example, patient lifting and support hoists, hoist motors, hoist straps, yokes, crossbars and their sling attachment hooks, and sling attachment joists of all designs, hoist framing and structures and the like, for both stationary and mobile as well as floor-based or overhead fixed patient lifting equipment. Each of the invention system components are hermetically sealed in PE and made sterile for single use as a disposable item.

In one embodiment, the invention draping materials and systems can comprise polyethylene-based fabric or any other single- or multi-layered material suitable for sterilization. Polyethylene (or PE as it is universally abbreviated), a particularly preferred example of a suitable material from which a drape according to the invention can be formed using any suitable process, is a nonwoven thermoplastic polymer consisting of long chains of the monomer ethylene classified into different categories based on density and branching of the polymer. Generally, PE used in the invention has a density between 0.915 and 0.925 g/cm3 (linear low density polyethylene, LLDPE), or alternatively between 0.910 and 0.940 g/cm3 (low density polyethylene, LDPE), or alternatively between 0.880 and 0.915 g/cm3 (very low density polyethylene, VLDPE). PE has long been used to make patient drapes, diapers, gowns and the like for use in sterile environments as it is amenable to sterilization processes by EtO gas and gamma ray radiation. The fabric can be formed using thermal energy, combinations of heating and cooling, and by RF and pressure. The PE draping of the invention is contemplated to comprise a multilayer composition wherein the individual layers can comprise latex free tissue paper, siliconized tissue paper, and PE. In related embodiments, the drape fabric is generally constructed to possess between 2 and 10 layers, more usually between 3 and 8 layers and most usually between 4 and 8 layers. Further, the PE drape material can also comprise polypropylene. Polypropylene is a single layer fabric and possesses many of the same qualities as polyethylene and is normally manufactured as a transparent material. It is also amenable to well used sterilization techniques. Although the primarily discussed material for use in sterile drapes of the invention is polyethylene- or polypropylene-based, any material whether single layer or multilayered useful for covering operating room equipment and being made sterile can be used.

Although the specific shape of the drape to be used over a particular operating room patient lift is variable, the drape system of the invention contemplates any shape capable of maneuvering over a patient lift device. For example, the material can be stretchable or alternatively non-stretchable. It can be opaque or clear. It can be single or multilayered. Or it can be overlaid with reinforcement webbing comprising any other or the same material. In one referred embodiment, the fabric is PE based fabric. In another embodiment the fabric can be constructed in a pleated or accordion fold style such that the fabric can be neatly collapsed or expanded similar to an accordion. Alternatively, the fabric can be unfolded (i.e., plain fabric). Alternatively still, the fabric can be any useful shape having any general or alternatively specific shape thereto. Cross-sectionally speaking, the shape at any given cross section can be circular, ellipsoid, square, triangular, pentagonal, hexagonal, septagonal, octagonal, etc. to any polygonal shape. With respect to one related embodiment, the fabric, whether accordion or plain styles, the sheet of fabric making up the plain or accordion styled form can be wrapped in a circle such that the opposite ends of the sheet are adjoining and fixed together forming a column or tube. On accordion style drape sheets, the opposite ends to be adjoined for fixing together are those that when the ends are affixed, the drape will form a tube and the accordion folds will allow expansion of the drape from a folded position to expand in the direction of the length of the tube as shown in FIGS. 1A, 1B, 1C and 1D. Specifically, drape material 10 can be formed into an accordion tube shape. Further, the drape tube can be fitted at one end with an elastic band 17 to cause the tube end to cinch up. The expandability of the elastic band is important in that it must be sized to allow the drape to be large enough at the opening to surround patient lift parts, particularly for floor based models. In preferred embodiments, the elastic has an expandability to reach a bag opening diameter of at between 24 and 36 inches. Alternatively, the elastic can be any size that will accommodate placement of the bag over a lift device.

Figure 1D:
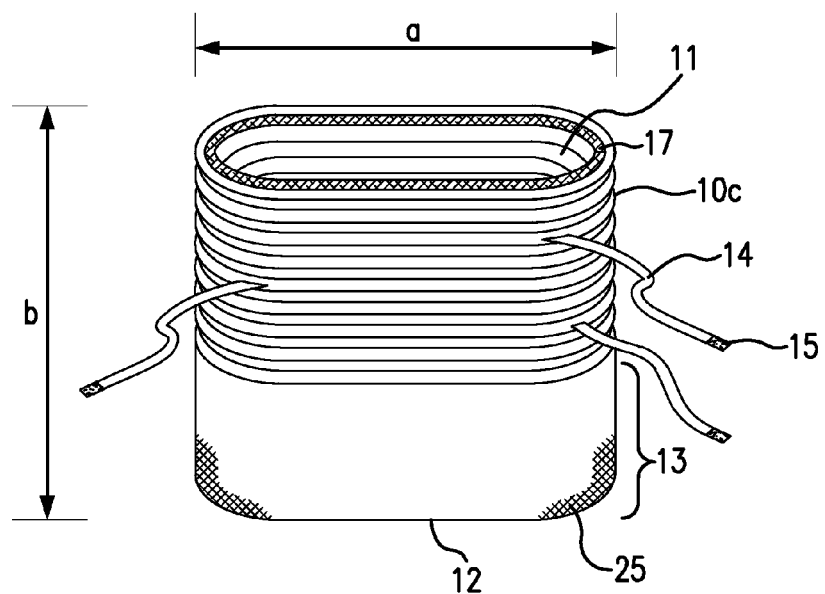

In another embodiment, the tubular drape, regardless of cross-sectional shape, and particularly whether plain or accordion, is contemplated to be open 11 at one end and closed 12 at the other (FIG. 1D). Further, the end that is closed is contemplated to be made of clear polyethylene or polypropylene or polyethylene plastic of a single layer 13 (FIG. 1D). Specifically, the clear portion comprises a length of the tube of between 6 inches and 24 inches, more usually between eight inches and 16 inches. The diameter of the clear section can be the same as or bigger than the accordion or plain section of the drape to which the clear section is attached. In preferred embodiments, the clear section is fabricated in a bag-like form and with a generally rectangular outline so as to fit easily over a linear crossbar. In alternate embodiments, the clear portion for fitting over a crossbar can be manufactured to be form fitted. Thus, depending upon the size of the crossbar, the clear portion can be manufactured to size. This clear portion provides for the technician's ability to see the patient hoist parts, such as the crossbar and yoke as the drape is manipulated over the lift apparatus. Additionally, the clear portion has formed with it PE reinforcement webbing 25 on lateral areas of the clear section.

Figure 2A:
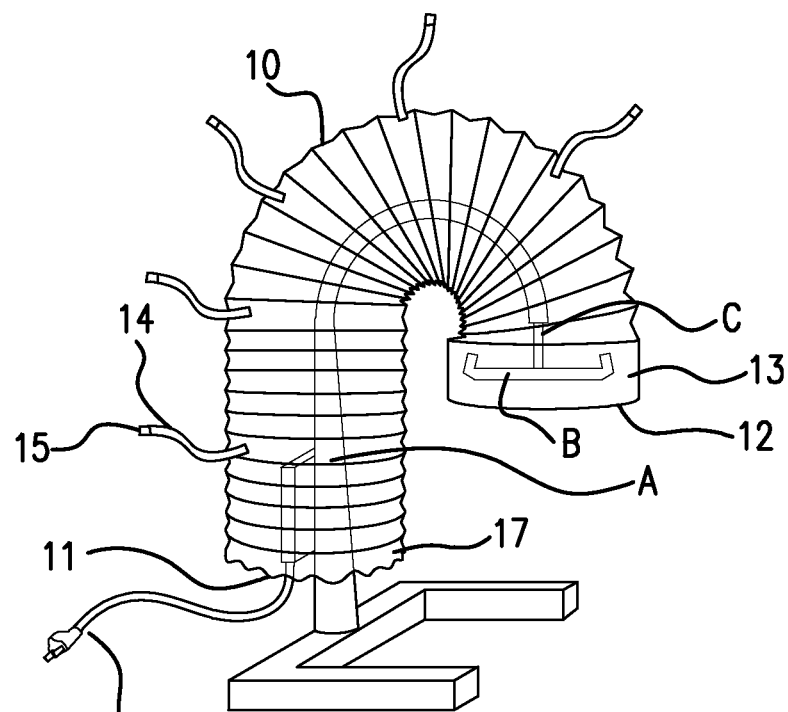
FIGS. 2A and B are drawings showing in FIG. 2A an accordion style drape 10 covering a mobile floor-based patient lifting hoist support structure and its electrical cord box and cord 75, A, the yoke and belt C, and the clear portion 13 covering the cross bar B of the hoist. Also shown are wrapping tabs 14 and adhesive 15.
Figure 2B:
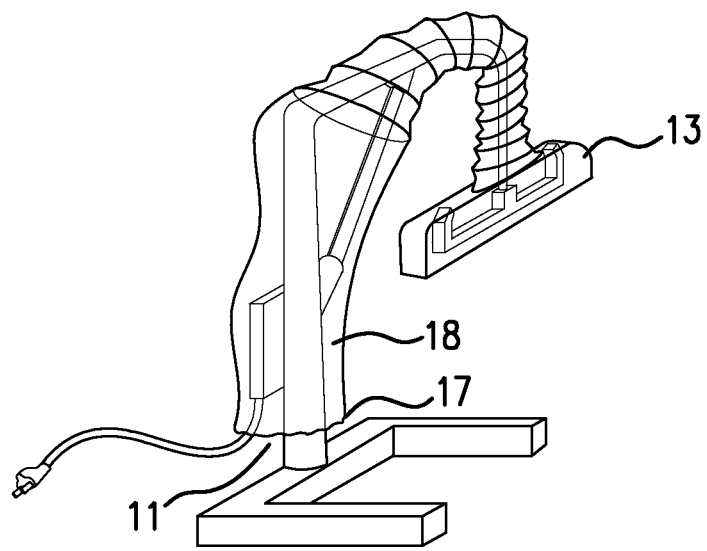
In FIG. 2B, the drape is a hybrid of plain and accordion style draping fabric wherein plain drape section 18 covers the lift vertical and hydraulic support arms of the hoist. The open end of the drapes 11 in both

In a preferred embodiment, dimensions in the sizing of the tubular formed drapes, whether of plain or accordion style, are contemplated to embody a size/dimension that will encompass any style of patient lifting apparatus, i.e., universal drapes. Specifically, for example, with floor based patient lifting systems such as shown in FIGS. 21 to 29, the sterile drape 10, as depicted in FIGS. 2A and B, can slide over the lift. In FIG. 2A an accordion style is shown covering the lifting support structure and electrical cord A, the yoke and belt C, and the cross bar B. Elastic band 17 allows the drape to cinch up against the lift frame and tabs 14 can be wrapped around the drape to gather excess material. In FIG. 2B is shown a hybrid drape comprising a plain section surrounding a lift that employs a hydraulic lift arm. Here the clear section can be dimensioned to surround this structure while the drape construction provides for the plain section becoming a narrower diameter and accordion shaped. In FIG. 2A the clear section 13 of the drape is shown same dimension as the accordion style while in FIG. 2B the clear section 13 is shown formed in a rectangular format.

Figure 3:
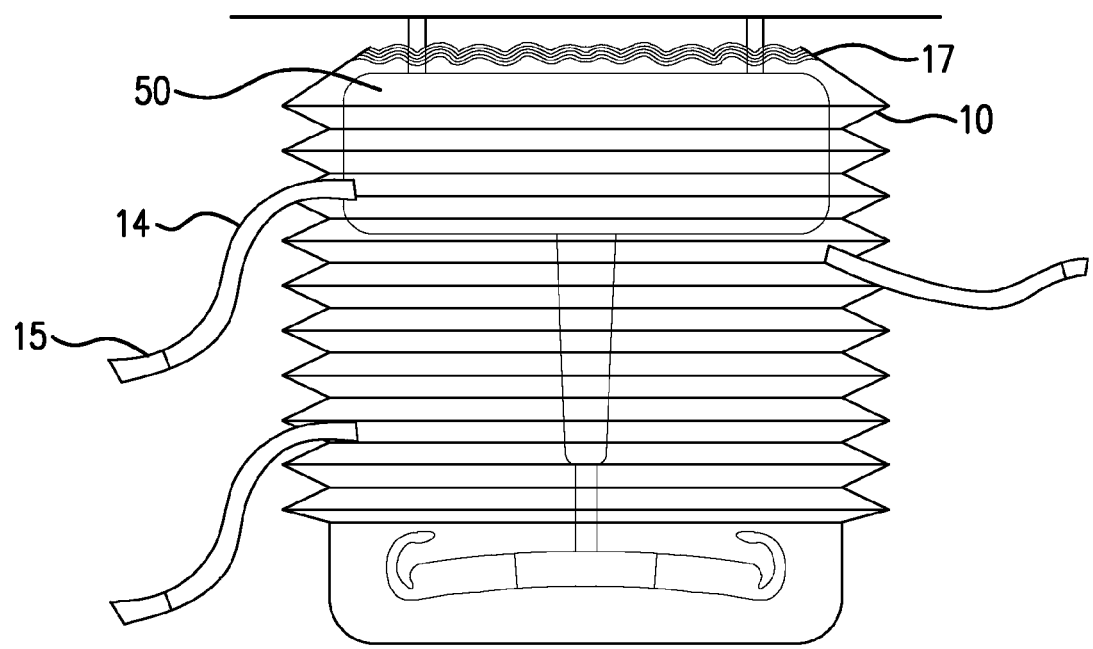
FIG. 3 is a drawing showing an accordion style drape covering a ceiling mounted patient hoist system. The drape covers the motor, belt and crossbar with the drape comprising a clear portion covering the crossbar. Alternatively, the drape can be completely clear covering the not only the crossbar but the entire lift motor and attachment points. Elastic or otherwise expandable band 17, shown fitting around the top of the ceiling mounted lift motor 50, holds the drape securely in place.
Figure 4:
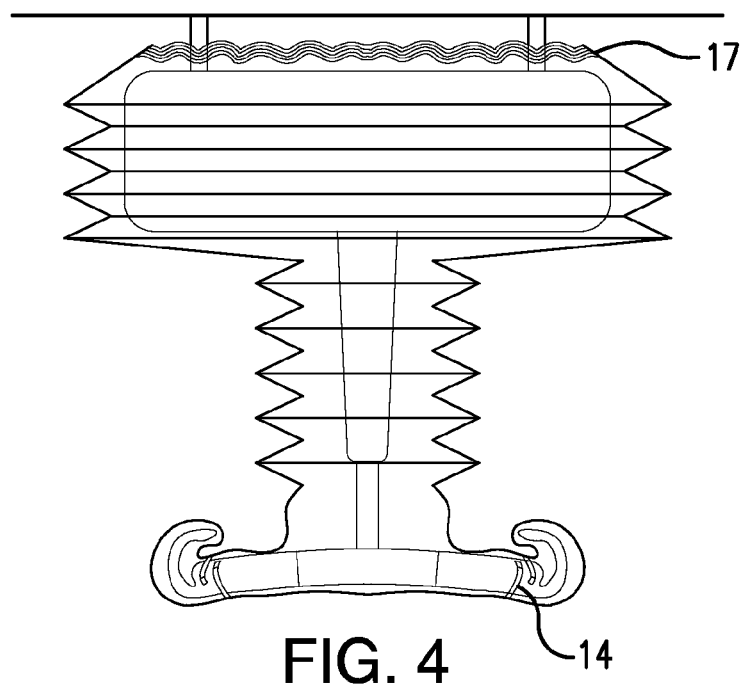
FIG. 4 is a drawing showing an overhead lift system draped in an accordion form fitted drape wherein the drape is held securely in place by elastic band 17. The drape is further wrapped with the adhesive ended tabs around the crossbar near the position of the sling hooks for keeping the drape in that section immobile.

With respect to sizes of the invention drapes, tubular dimensions can be various measurements depending primarily upon the bulk of the lift design. For steel/aluminum frame floor based lifts the accordion tube must fit over the support arm and the yoke, belt and crossbar, and where present a hydraulic piston arm. In a particularly preferred embodiment, the tubular diameter required can depend upon the construction design of the crossbar as well. For example, the clear section can either comprise a bag shape of dimensions similar to the main drape accordion section or it can be rectangular and of a larger dimension than the drape tube. Dimensions for covering such a lifting device generally require about between 10 inches and 36 inches of internal diameter for clearance around the various parts of the lifting device. More usually, the useful dimensions for tubular diameter of the drape is between 12 and 30 inches. For large crossbars intended for lifting a patient horizontally, the crossbar framing can be two to three feet wide and five to six feet in length as opposed to a simple linear crossbar having measurements between six and 36 inches. The dimensions of the maximum tubular length of either a plain or accordion style drape is determined by the linear size of the lifting device's support arm and belt/yoke and crossbar length. Generally, for floor based hoists, the tubular length will be between three and 16 feet, more generally between four and 14, still more usually between seven and 13 feet. For overhead lifting systems wherein the extendable belt provides the necessitated length, the tubular length required for the drape is generally between one and eight feet and more usually between two and seven and most commonly between two and four feet. The shorter length necessary for an overhead lift arises from the fact that the typical operating table is 34 inches from the ground and only the crossbar, and belt need covering as well as the generally rectangular box shaped lift motor. For overhead or ceiling-based patient hoists the accordion drape can fit about the motor, yoke and crossbar as depicted in FIG. 3. The elastic band 17 provides a secure fit of the drape with the top of the motor housing 50. The accordion excess drape material can be gathered and held in place by polyethylene strips comprising an adhesive applied thereto as depicted in FIG. 4. Specifically, the tabs associated with the drape for an overhead lift system as well as for a floor based system can be placed strategically to function by keeping certain portions of the drape in place and immobile. For example, tabs 14 can be manufactured into the clear portion of the drape near the sling hook portion of the crossbar (FIG. 4). The tabs can be snuggly wrapped around the bar to keep the drape material in the crossbar hook from shifting which further provides for avoidance of stress and strain on the sealed drape.

Figure 5:
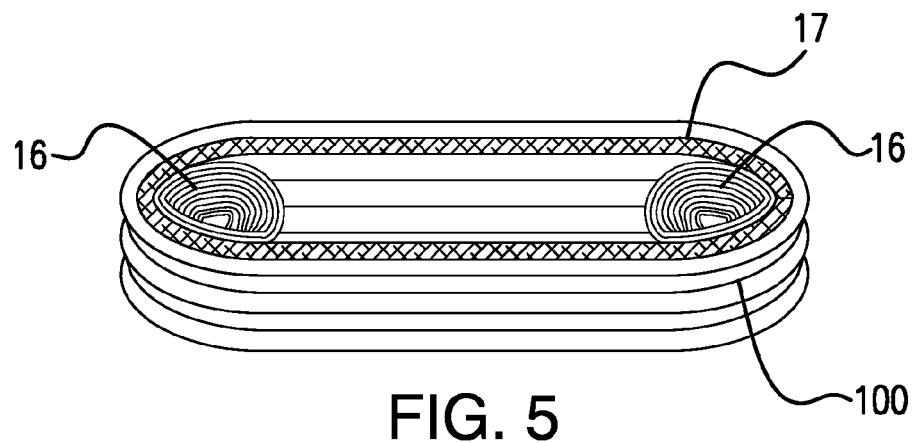
FIG. 5 is a drawing showing the open end of the tubular drape 10D with elastic banding 17 and hand manipulation pockets 16. The drape is shown in a ready to use collapsed position.

Other features of the drape design contemplates advantages for manipulating the drape about the lifting device parts to aid maintenance of a sterile environment. Specifically, the drape in sterile packaging is removed from sterile wrapping wherein the operation technician places his/her hands in pouches 16 formed at one end of a collapsed drape tube as shown in FIG. 5. As an example of application, the operating room surgical technician or orderly would prep the lifting device by opening the package containing the sterile drape, placing his/her gloved hands into pockets 16 formed in the inside of the open end of the drape, then keeping the drape in a collapsed or folded state initially, the technician pulls the drape around the crossbar and yoke then up, and while allowing the accordion drape to unfold, pull the drape over the lift support beam and down towards the floor touching only the inside pockets on the non-sterile machine side of the fabric resulting in a draped patient hoist as shown in FIGS. 2A and B. In this process the technician has only had to touch the leading circumference of the tube with hands in the pouches with the final stopping point of covering being near the lower part of the support where elastic band 17 causes the drape to cinch up on the lift support. The technician can then gather up the excess drape material, whether plain or accordion, using the straps having adhesive applied to the outer end portions thereof. This process can also be used to cover over head lifts as depicted in FIG. 3. Where necessary the excess drape material is collected by winding the PE tabs 14 (see FIGS. 2A, 2B and 3) around the support beam and lift parts (and for overhead systems the motor and lifting belt), and adhering the tabs 14 to the drape material with adhesive portions 15. In this configuration, the entire patient hoist is covered and the crossbar and its attachment hooks are visible through the clear PE.

Figure 6A:
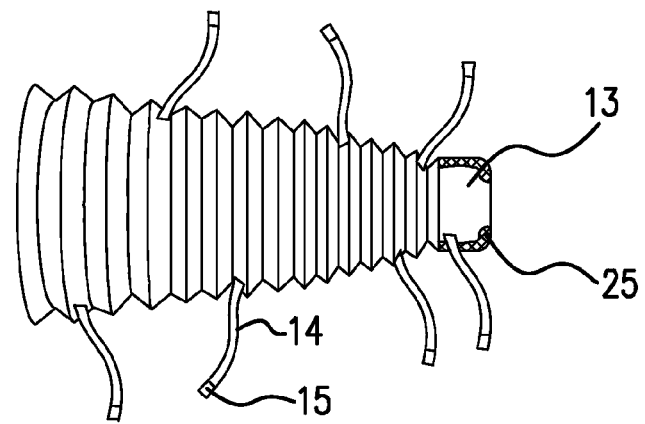
FIGS. 6A, B and C are drawings showing various embodiments of the invention.
Figure 6B:
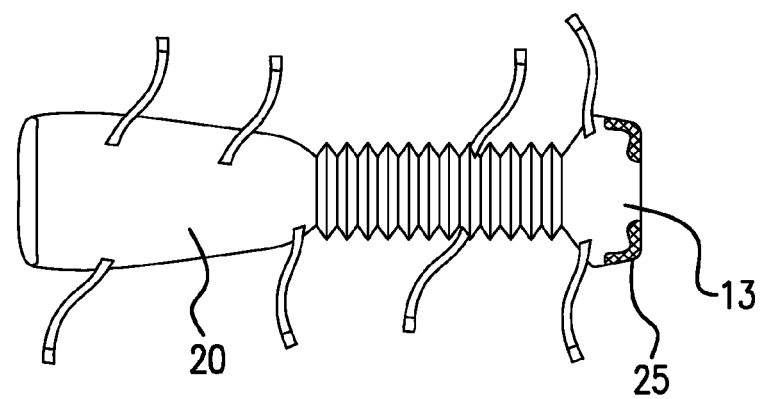
FIG. 6B depicts a plain drape design extending from the opened end and subsequently transforming to an accordion style narrower tube. The narrow section is designed to have at least a 2 inch to 4 inch greater diameter than the lift belt width to accommodate insertion of the crossbar. Both FIGS. 6A and 6B drape configurations include a clear portion at the closed end of the drape with reinforcement webbing 25 along opposing sides thereof.
Figure 6C:
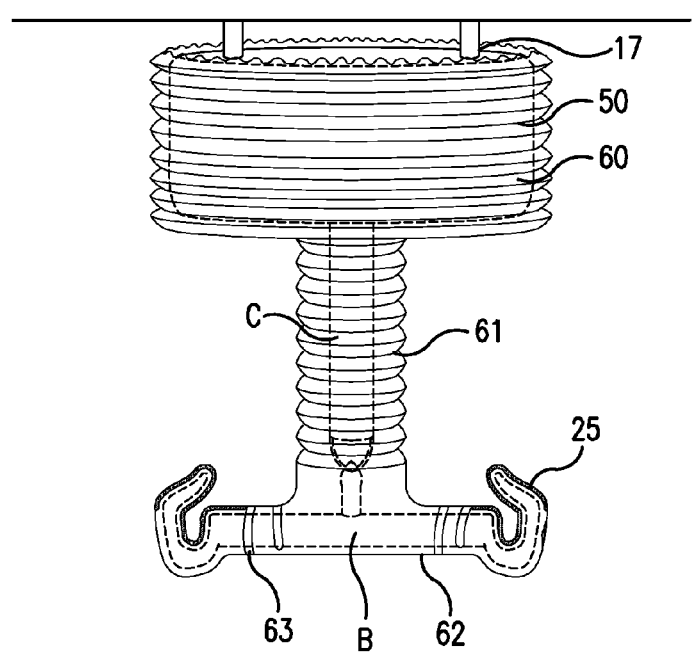
In FIG. 6C is depicted a shaped drape for an overhead or ceiling mounted lifting motor cover 50 wherein the portion 60 meant to cover the motor cover 50 is accordion sized for the motor cover 50 and the portion 61 for covering the yolk and hoist band C is narrow and accordion, while the portion covering the crossbar is clear with reinforcement webbing. The depiction further shows tabs banded around the crossbar immobilizing the drape in the area near the sling attachment points.

In a further embodiment, concerning the shape of the accordion tube drape, or alternatively a plain drape tube, one end of the tube can be of a greater diameter than The other end of the tube as depicted in FIGS. 6A and B. In such embodiment, generally, the larger end comprises the opening wherein the technician grasps, through use of the pockets, the drape and can channel it over the lifting apparatus structure, the diameter of the drape tapering to a smaller end at the end where the yoke and crossbar attach. In still further alternate embodiments, the drape design can be formed to accommodate various styles of floor mounted hoists such as depicted in FIGS. 21-29 with a plain and accordion hybrid type drapes. For example, as shown in FIG. 2B the open end portion for leading over the hoist boom and hydraulic ram can be plain drape tapering or otherwise switching to an accordion format at the portion leading up to the upper hydraulic press fitting at the lift boom. The embodiment depicted in FIG. 6B shows the plain section transforming to an accordion tube format that will accommodate the patient lift of FIG. 2B that has a hydraulic arm. Further, in FIG. 6C is depicted another embodiment of the drape wherein it is fitted to the hoist motor housing. Generally, the sizes of ceiling mounted hoists range between 13 inches square and six inches in height to rectangular shapes about 30 inches long by 6 inches wide by 12 inches high. As depicted in FIG. 6C, the drape covers motor housing 50 closely and is kept in place by elastic band 17. The section covering the belt C is narrow tubular 61 while the clear section 62 is formed, in this example, as a rectangle fitted with reinforcing webbing 25 and tabs 63 cinched around the crossbar.

As previously stated, the invention contemplates attachment to the drape material, whether plain or accordion tubes, of periodic or spaced polyethylene (or any other material) tabs of varying lengths but generally between three inches and 24 inches in length, and more typically between six and 18 inches, and comprising at the distal ends polyethylene or other plastic covered adhesive, such as for example, tape, glue, and the like. In a particularly preferred embodiment, the tabs are useful for wrapping around and gathering up excess drape material following application of the sterile drape over the operating room machine, such as for example, a patient hoist, and maintaining the bunched excess drape material in position by removal of the covering of the adhesive and contacting it back to the drape. In a particularly preferred embodiment, the tabs can be specifically located as well along portions of the clear portion of the drape covering the crossbar. As disclosed above, the tabs can be located near the hook portions of the crossbar. For crossbars containing multiple hooks, as disclosed below (FIGS. 11, 12, 30 and 31), tabs can be located so as to be able to cinch the drape onto the crossbar anywhere along the bar length. For uses over a crossbar with at four hook sets, for example, the drape can have at least eight tabs.

Figure 7:
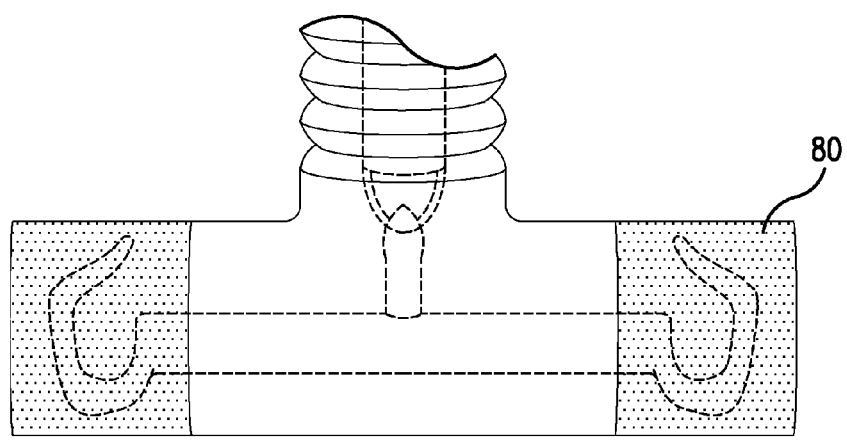
FIG. 7 shows additional embodiments of the crossbar section of an alternate drape reinforcement style wherein the reinforcement webbing 80 is applied to the entire end of the clear section of the drape that covers the terminal portions of the crossbar.
Figure 31:
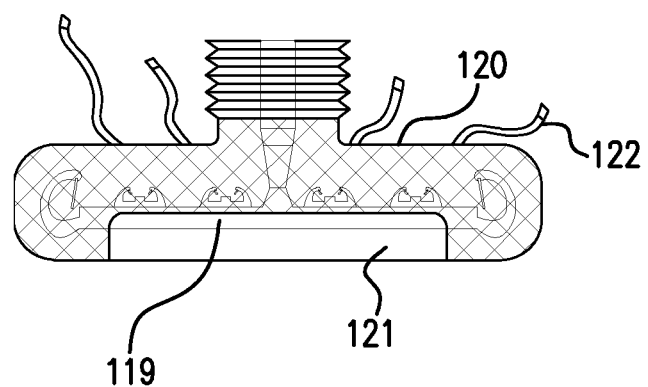
FIG. 31 depicts one embodiment of the crossbar section of the drape wherein the top and end portions of the clear section comprises reinforcing webbing.

In further alternate embodiments, the clear portion of the drape covering the crossbar can be formed to have PE reinforcement webbing covering the ends of a formed bag such that the entire end hook section will be protected from undue stress (FIG. 7). Further still, as shown in FIG. 31, the entire top and opposing ends 120 of the clear portion 121 of the drape covering the crossbar 119 can be constructed with reinforced webbing to accommodate crossbars with multiple sling hooks according to the instant invention. Additionally, the tabs 122 can be added for use in immobilizing the drape against the bar.

Figure 8A:
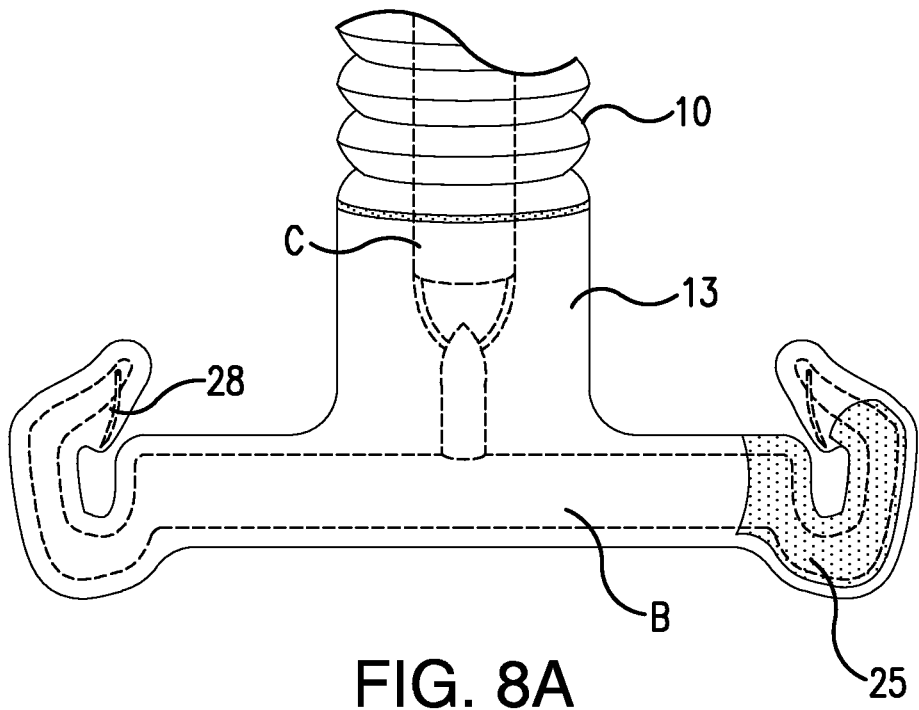
FIGS. 8A through G are drawings showing detail of the drape 10 about the crossbar and the crossbar hook and as it engages a reinforced PE loop of a sealed sling of the invention.
Figure 8B:
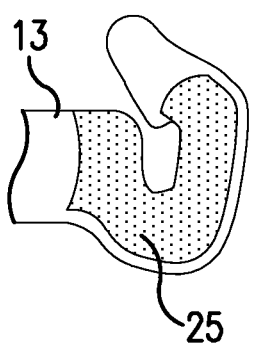
Figure 8C:
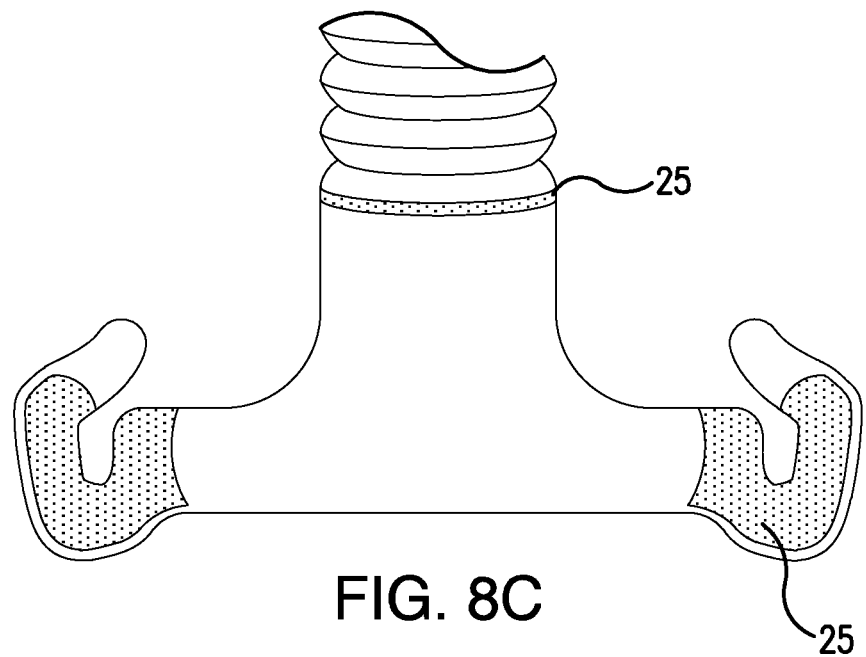
Figure 8D:
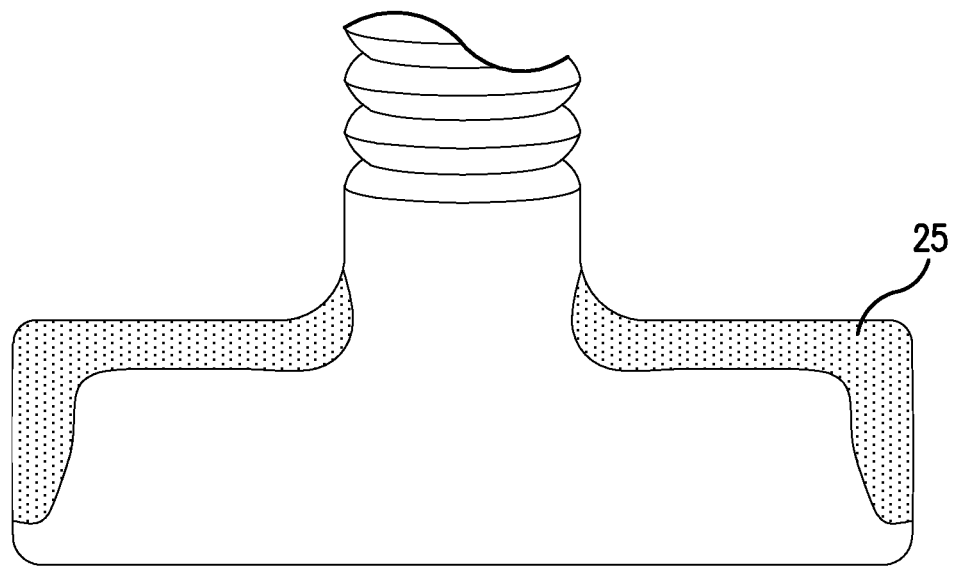
Figure 8E:
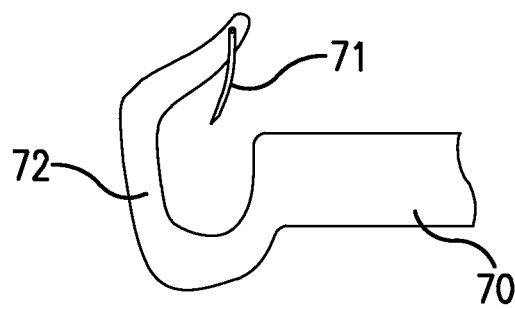
Figure 8F:
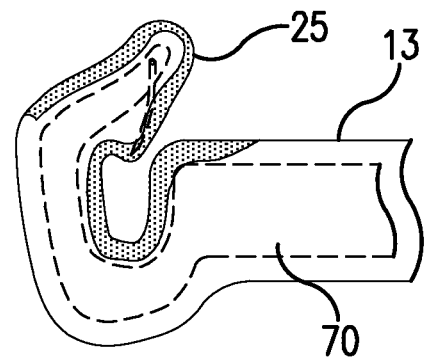
Figure 8G:
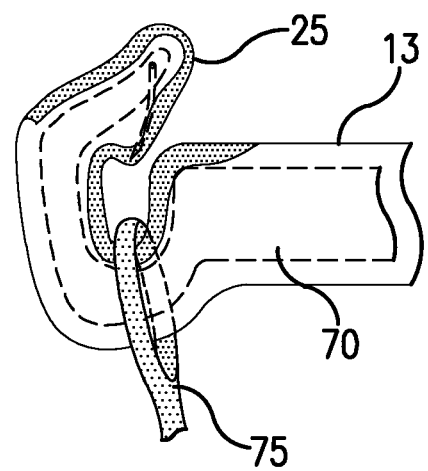

In FIGS. 8A to G, greater detail is disclosed on the construction of the drape clear section that covers the crossbar and contacts the sling loop. In FIG. 8A, a close-up of a crossbar B inside a drape clear section 13 is shown wherein the reinforcement webbing 25 is constructed into the clear portion at areas designed to contact the crossbar hook. FIG. 8B is a close-up of the clear drape section formed in conformation with a hook. In FIGS. 8C and D are depicted rectangular shaped clear sections that have the reinforcement webbing along the upper and opposing side areas. FIGS. 8E to G depict a series of the hook 72 of the crossbar 70 with clasp 71 wherein in 8F the drape is formed and nestled inside the hook cradle and 8G depicts the loop 75 on the draped hook with the reinforcement webbing contacted therebetween.

Figure 9A:
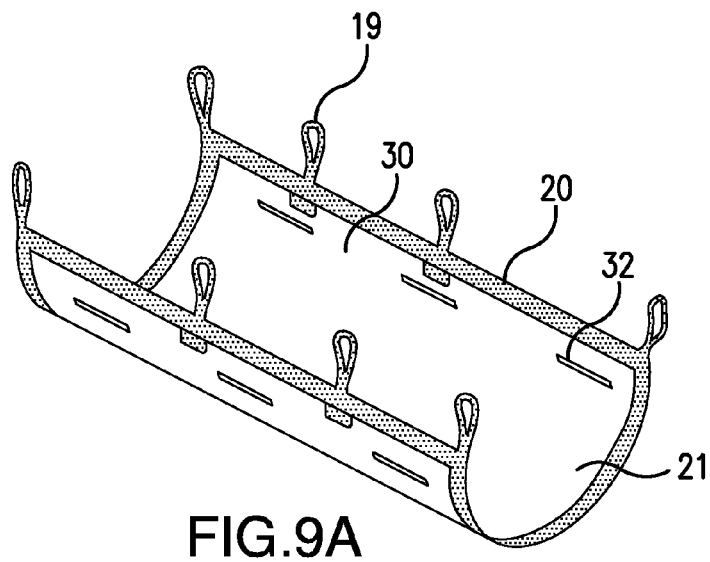
FIGS. 9A, 9B and 9C are drawings depicting and example sling and patient tie down strap.

In further embodiments, the invention comprises sterile disposable patient support slings for use in conjunction with the sterile drapes for further use in supporting patient body and body parts during surgical procedures under sterile conditions. The slings are contemplated to comprise polyethylene-sealed sterile sling assemblies further comprising polyethylene reinforced loops of generic and various lengths and sizes and positions. In a related embodiment, the polyethylene material can be applied to the inside of sling loops and inside of the yoke assembly of the typical hoist to provide strength and prevent tearing during patient lifting and repositioning. In a particularly preferred embodiment, the loops are formed of reinforced drape material incorporated and/or fused into the polyethylene drape for strength and prevention of tearing at the contact point between sealed sling loop and sling drape material. Reinforcing material can be any useful material for strengthening the fabric. In a preferred embodiment the material is polyethylene- or polypropylene-based. For large slings, the reinforced loops can be located at any position around the outer edge of the sling. For example, a sling made sterile by sealing it within PE drapes and for holding a prone human body can have sling loops spaced along opposite edges of the sling fabric as shown in FIGS. 9A and B. Generally, for whole body slings there are hanging loops at each corner of the sling and three to four loops strategically placed in a spaced format along opposite sides of the sling. In one embodiment, a sling can have three internal side loops, for example. In this example, with a body sling measuring 70 by 43 inches, the first internal side loops can be 12 inches from the corner and nine inches from the center side loop.

Figure 9C:
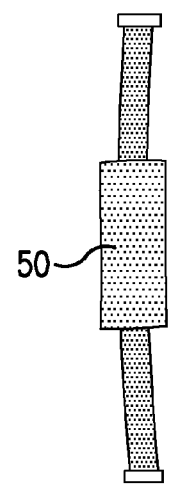
Figure 9B:
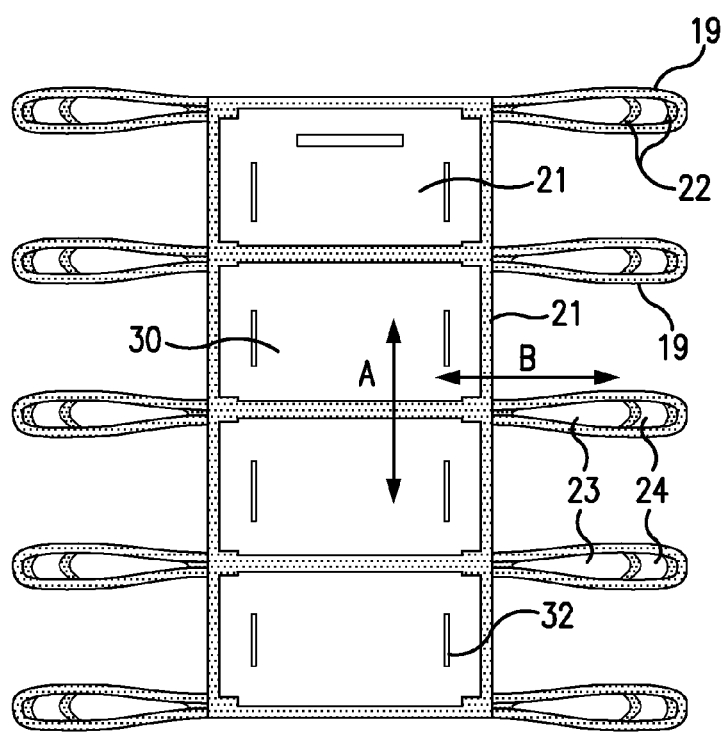

Slings can be made for carrying any amount of weight typically encountered during surgical procedures. Such weights can run anywhere between 15 to 660 pounds. Thus, the slings must be robust in their capacity to carry a substantial load. As depicted in FIGS. 9A and 9B, a full body sling 30 and its loops 19, for example, can be covered completely in PE draping 21. As detailed in FIG. 9B the covered sling 30 can be reinforced with PE webbing well known in the art across the body of the sling and along the edges and covering the loops. Although the FIG. 9B depicts the reinforcement webbing covering the entire sling loop, in an alternate embodiment the sling loops can simply be covered in PE drape material and only the portions 22 that are intended to contact the crossbar hook can be covered by the PE reinforcement webbing. Further, the sling can be manufactured with slots 32 spaced along the length of the sling. Slots 32 provide for the ability to run a belt through the body of the sling for the purpose of strapping down a patient firmly while on the operation table and still be on the sling. Typically, a, rubber, elastic, nylon or muslin material is used with a padding for patient comfort while securely strapped down to the operating table. As depicted, the slots are spaced along the sling so that the patient can be "locked" down at the ankle, knee, hip and shoulder. In a further preferred embodiment, the invention system includes a patient tie down strap 500 (FIG. 9C) with padding also hermetically sealed in PE. Such belt can be included in the sterile packaging containing the sling. In preferred embodiments, the belt must be robust enough to secure a patient weighing as much as 400 to 600 lbs.

Figure 10A:
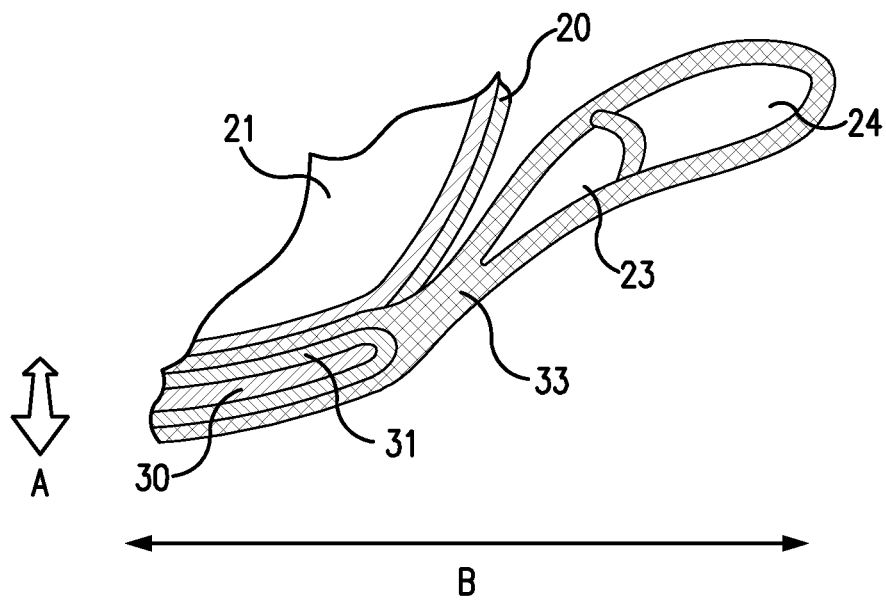
FIGS. 10A and 10B are drawings depicting aspects of the sealed sling loop of the invention.
Figure 10B:
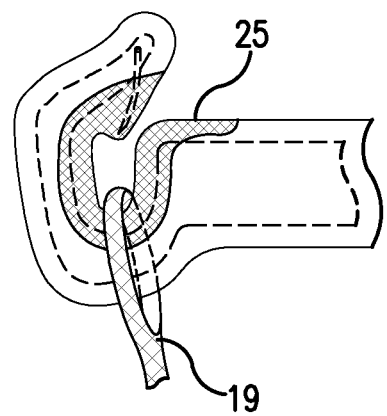
Figure 12A:
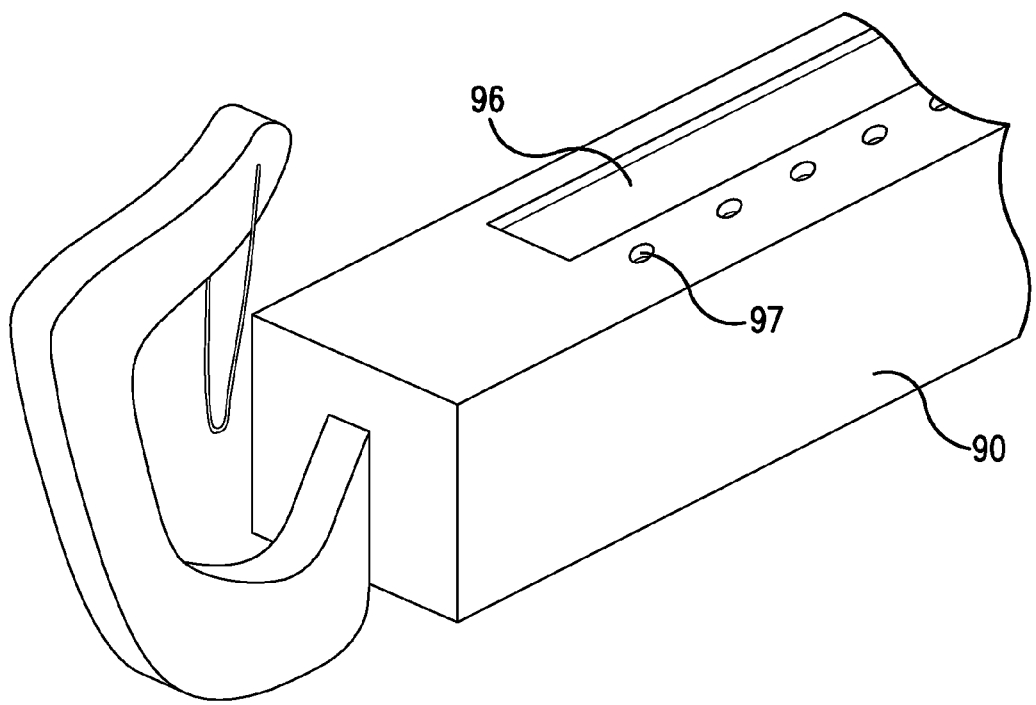
FIGS. 12A, B and C are drawings that depict detail of the internal shuttle cock sling hook.
Figure 12B:
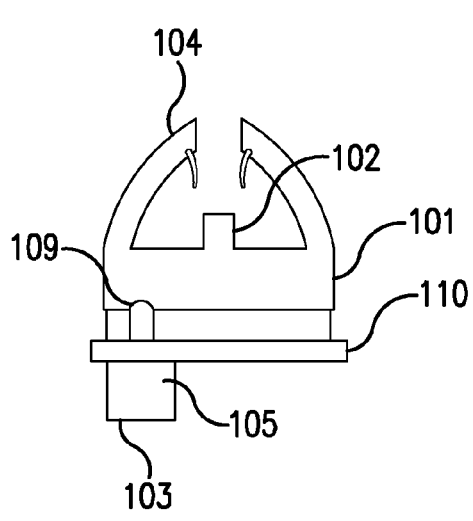
In FIG. 12B is a cross-sectional drawing of the shuttle cock 101 comprising base plate 110, keeper button 109 seated in spring box 103 and internal keeper button spring 105. The keeper button 109 and spring box 103 can be positioned anywhere on the base plate but in a preferred embodiment, the button can be located centrally on the shuttle cock such as aligned with the center of the shuttle cock post 102.
Figure 12C:
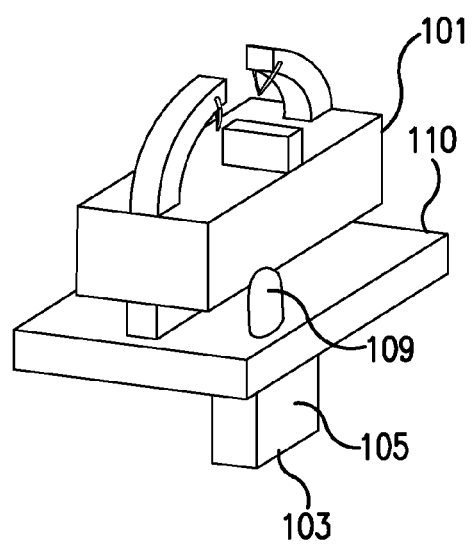
FIG. 12C provides additional detail in three quarter drawing showing shuttle cock 101, base plate 110, button 109 and spring and housing 105 and 103, respectively.
Figure 13:
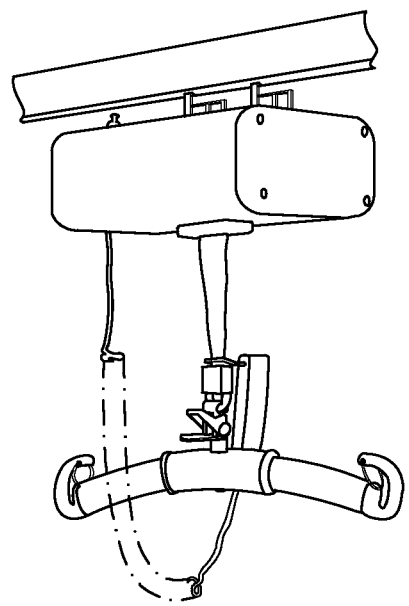
FIG. 13 is a picture showing a typical ceiling mounted or overhead lifting assembly.
Figure 14:
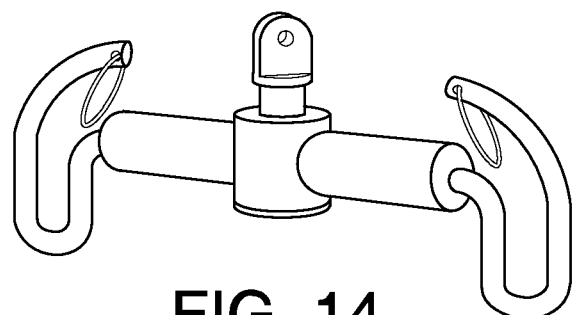
FIGS. 14-20 are pictures showing various crossbar models used with both floor based mobile and overhead mounted patient lifting systems that can be covered by the sterile drapes of the invention.
Figure 15:
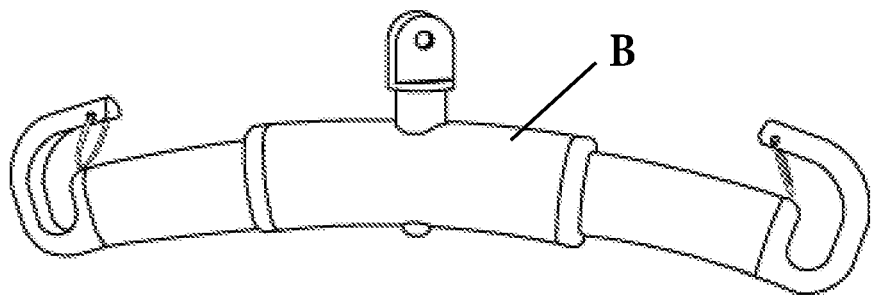
Figure 16:
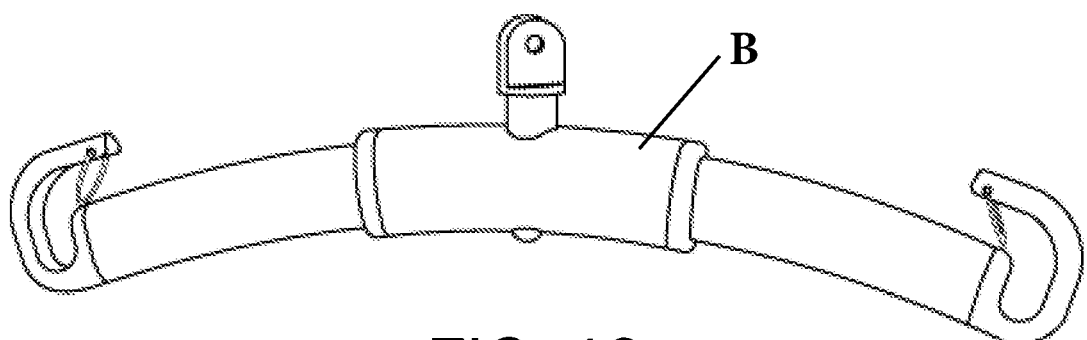
Figure 17:
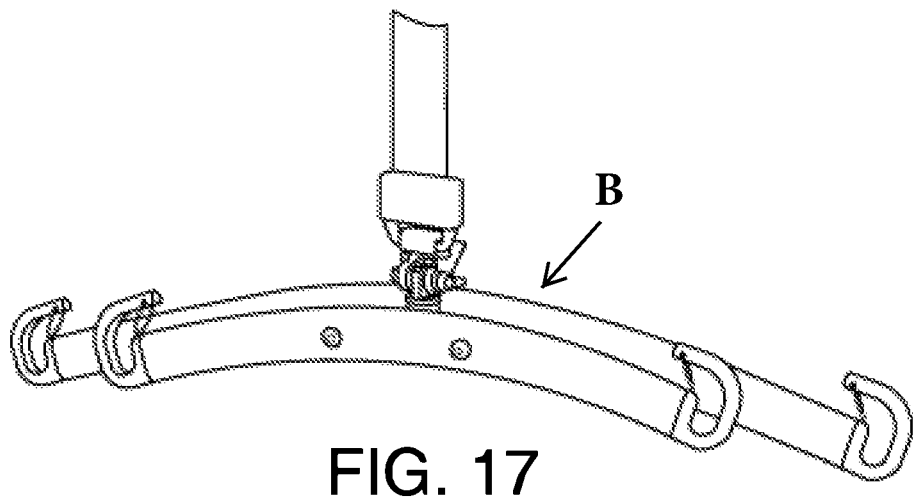
Figure 18:
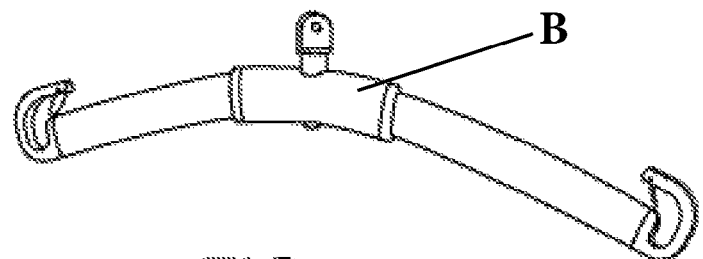
Figure 19:
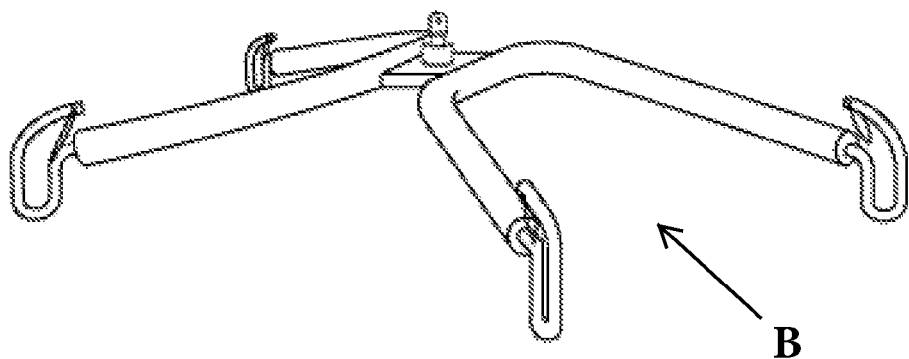
Figure 20:
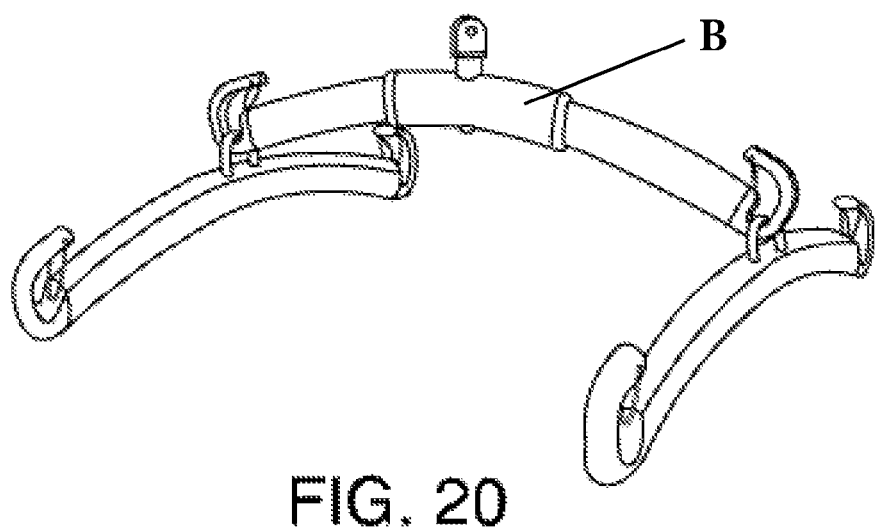
Figure 21:
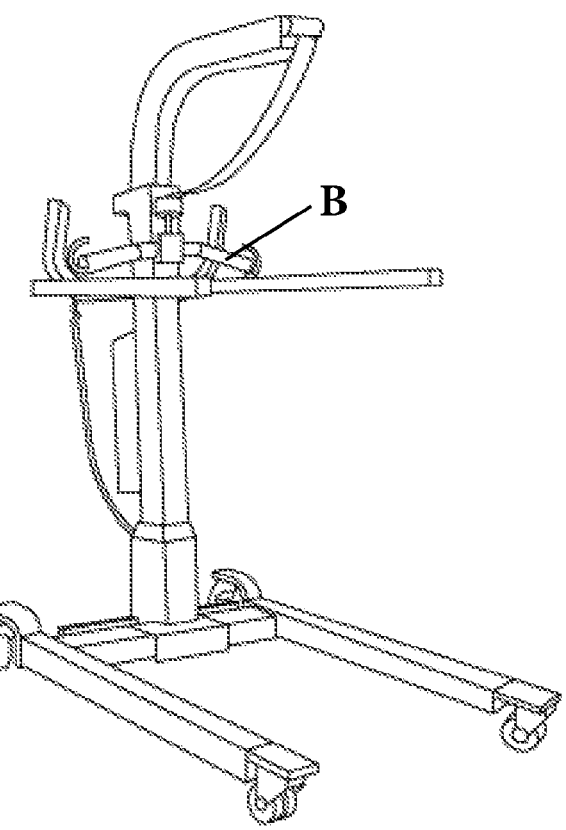
FIGS. 21-29 are pictures showing various models of floor based lifting devices that can be covered by the drape systems of the invention.
Figure 22:
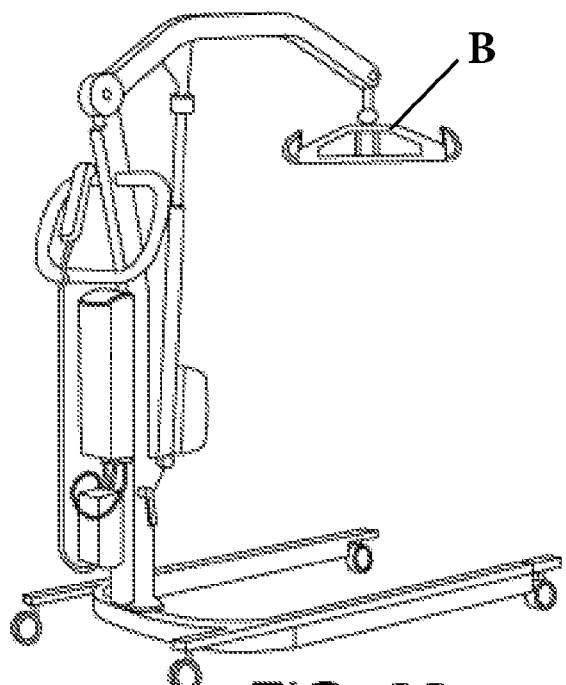
Figure 23:
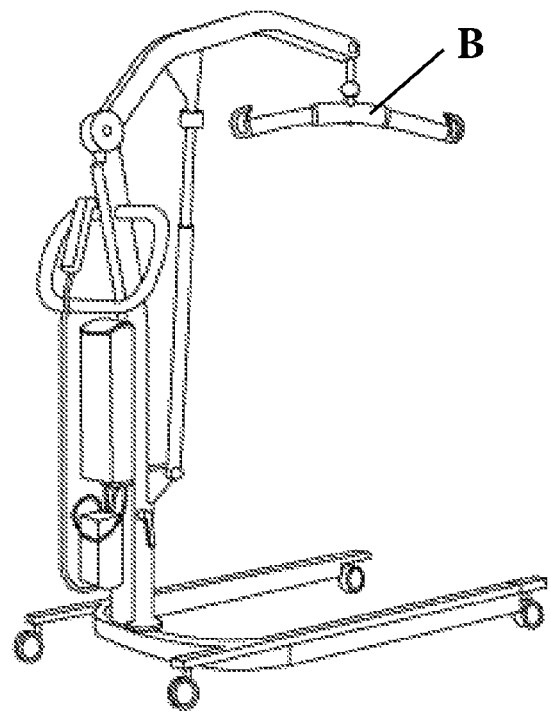
Figure 24:
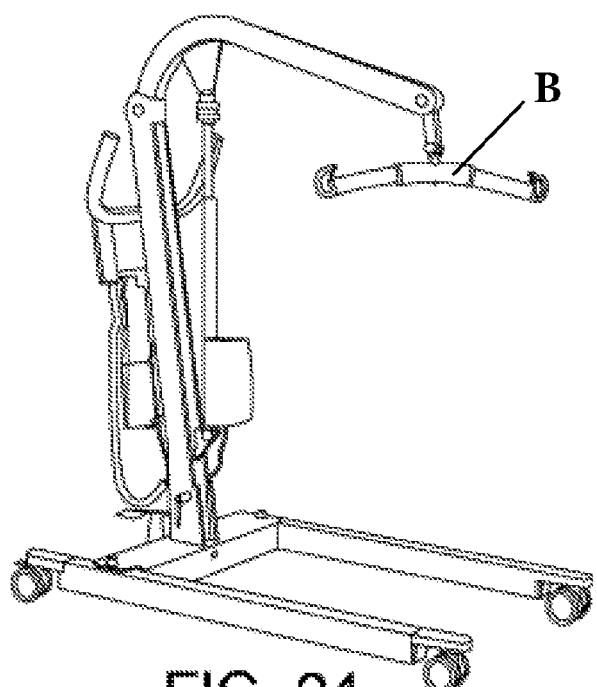
Figure 25:
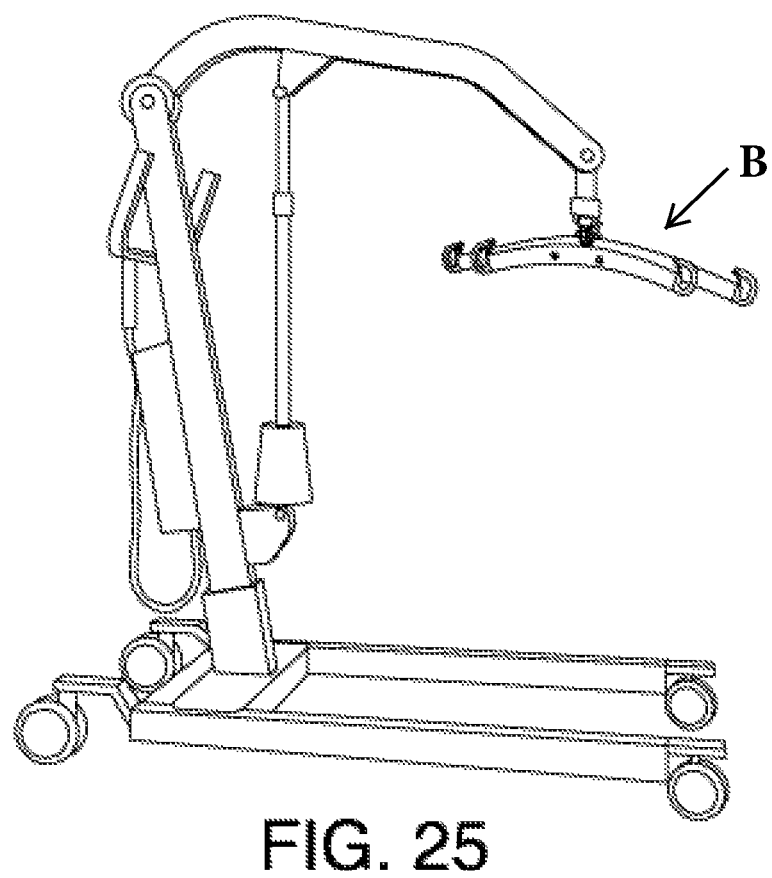
Figure 26:
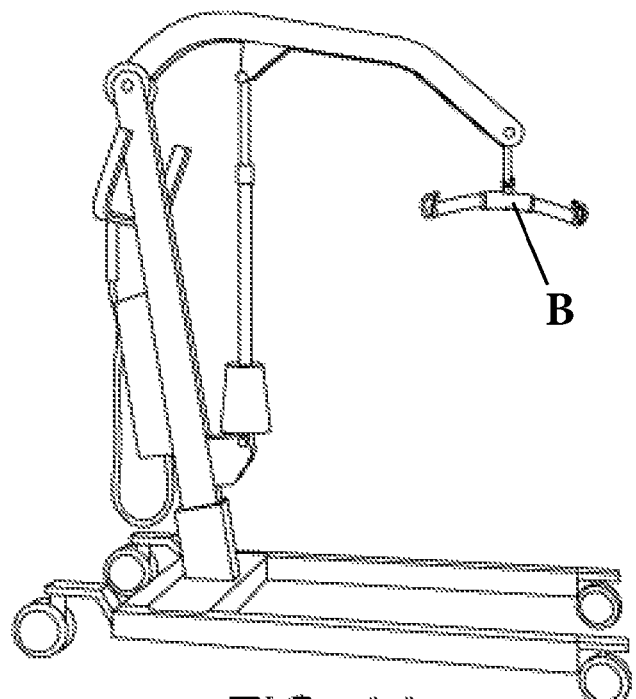
Figure 27:
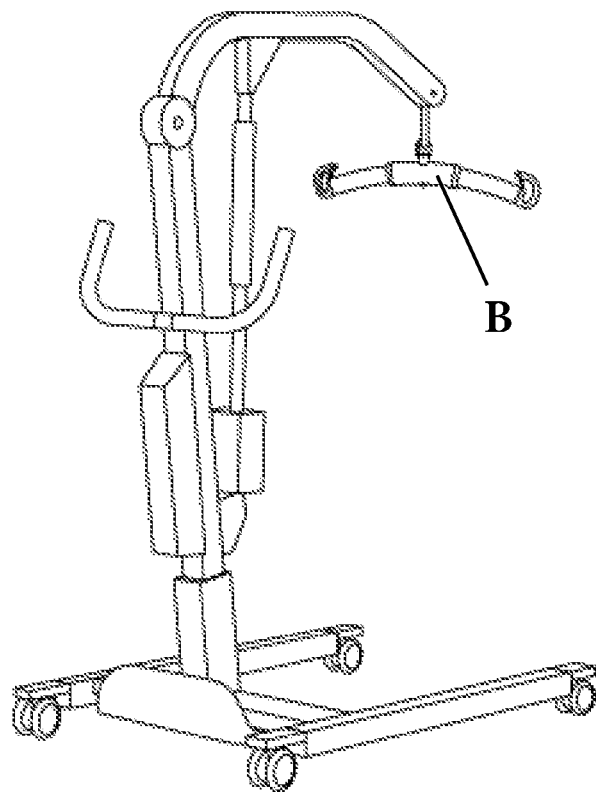
Figure 28:
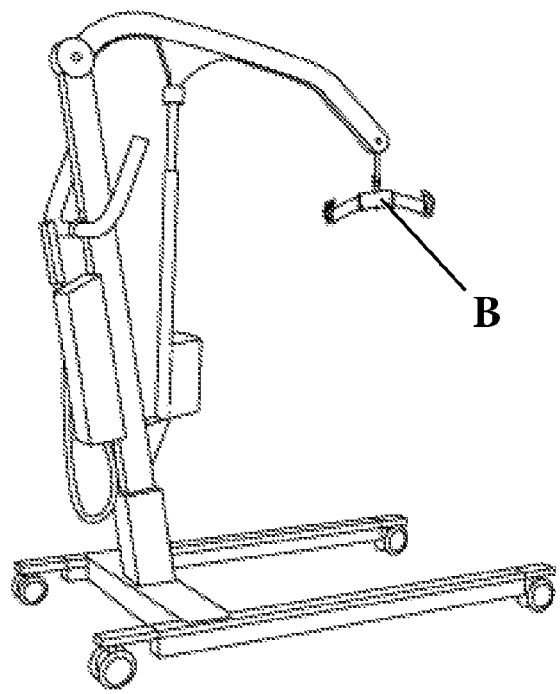
Figure 29:
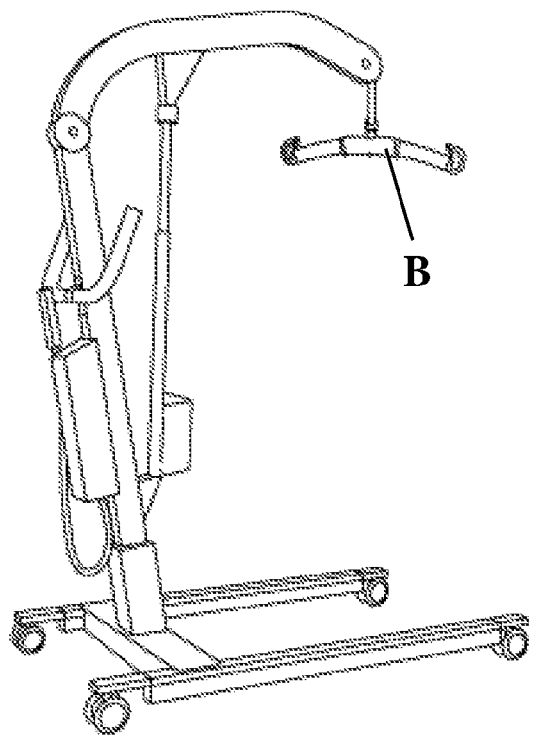
Figure 30A:
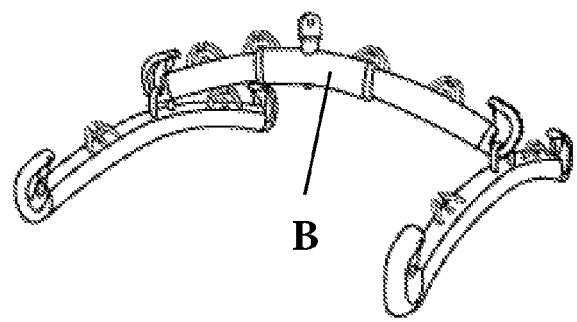
FIGS. 30A, B, C, and D are drawings showing alternate embodiments of crossbars constructed with internal adjustable (or not) sling hooks.
Figure 30B:
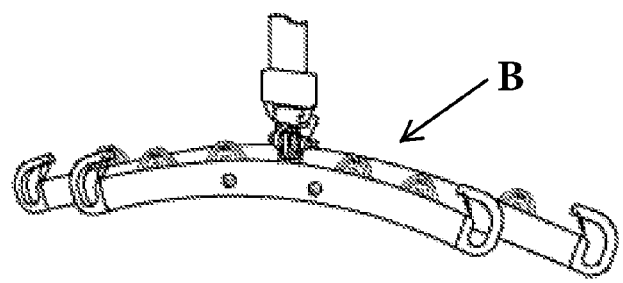
Figure 30C:
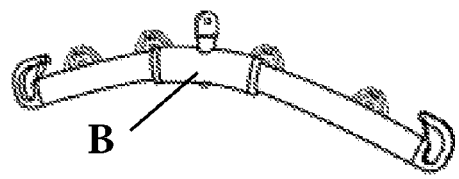
Figure 30D:
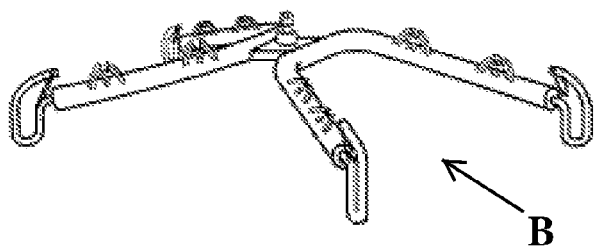

FIGS. 10A and B show additional details of the sling and loop. In FIG. 10A, a partial cross section is depicted from a three quarter view of a sling. Sling material 30 is completely covered in PE draping 31. The PE draping has over it, or otherwise formed with it, reinforcement webbing along the sling edges 20 and over the sling loops. In one alternate embodiment, since the sling loops are already made of reinforced webbing, and therefore only need to be covered by the sterile PE drape, the reinforcement webbing applied to the loops can be place predominantly only within the interior part of the loops, namely the area that would contact the crossbar hook cradle, i.e., location 22 of FIG. 9B. FIG. 10B shows the loop hooked to a crossbar arm with the reinforced areas 25 of the drape contacting the loop 19.

Figure 32A:
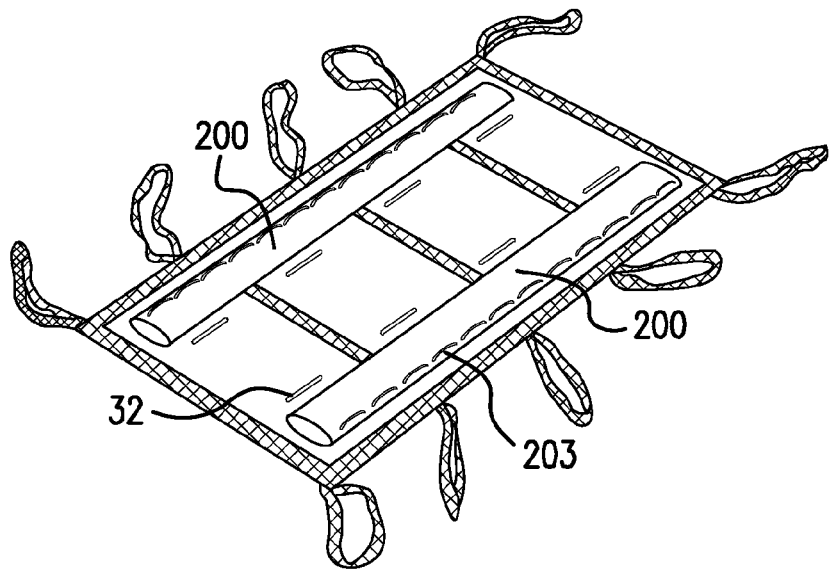
FIGS. 32A, B and C show a sling with elongate pouches molded along the length of the top of the sling.
Figure 32B:
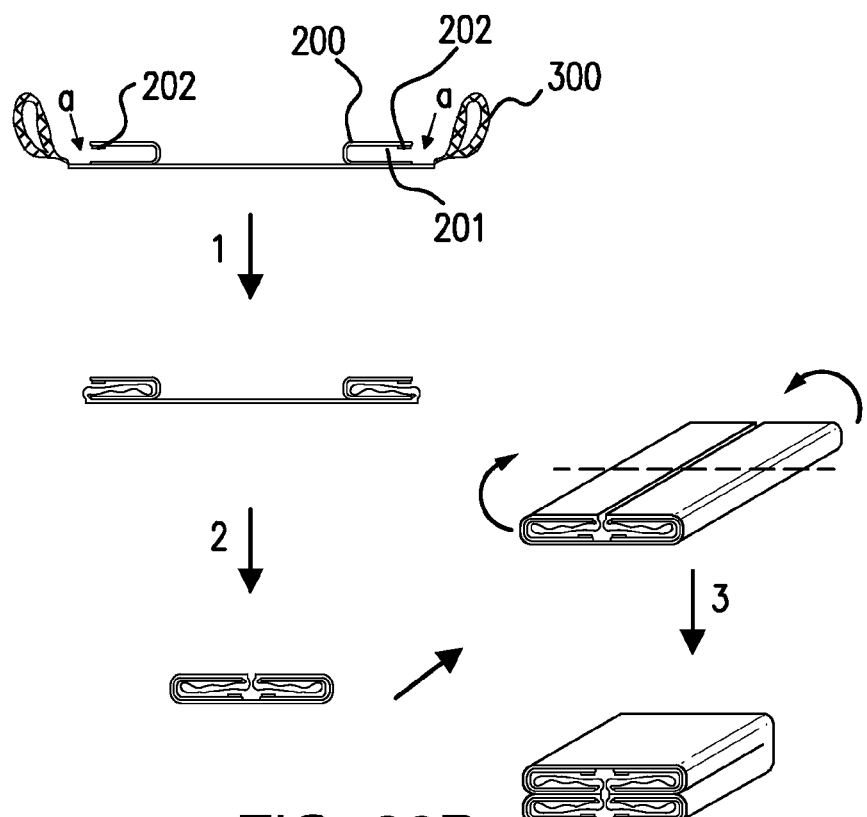
Figure 32C:
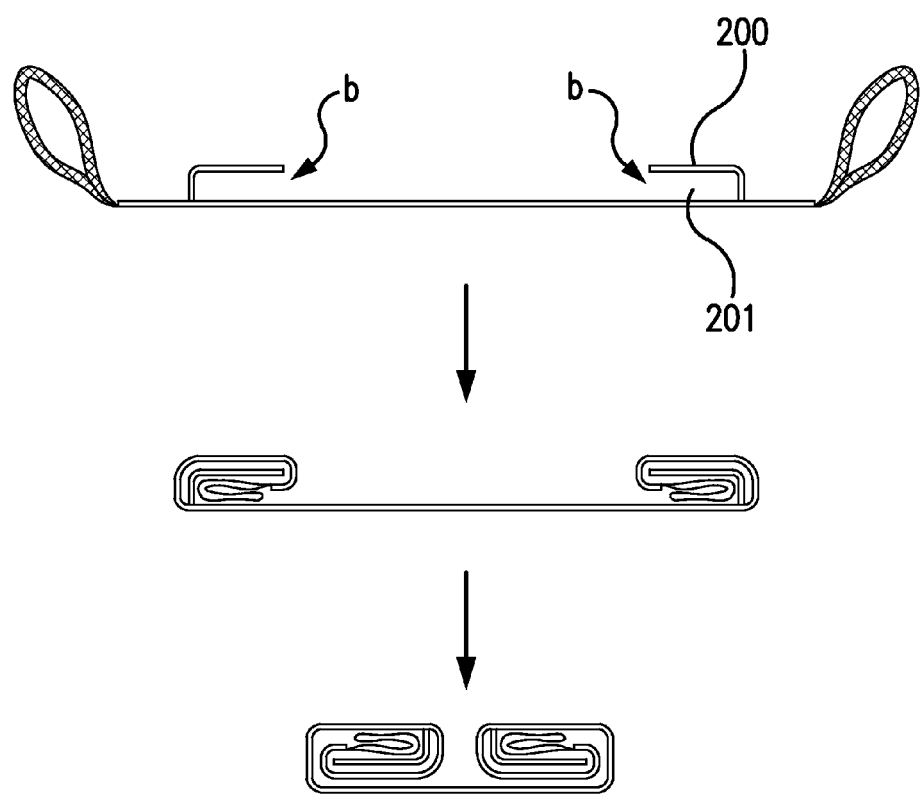
Figure 33:
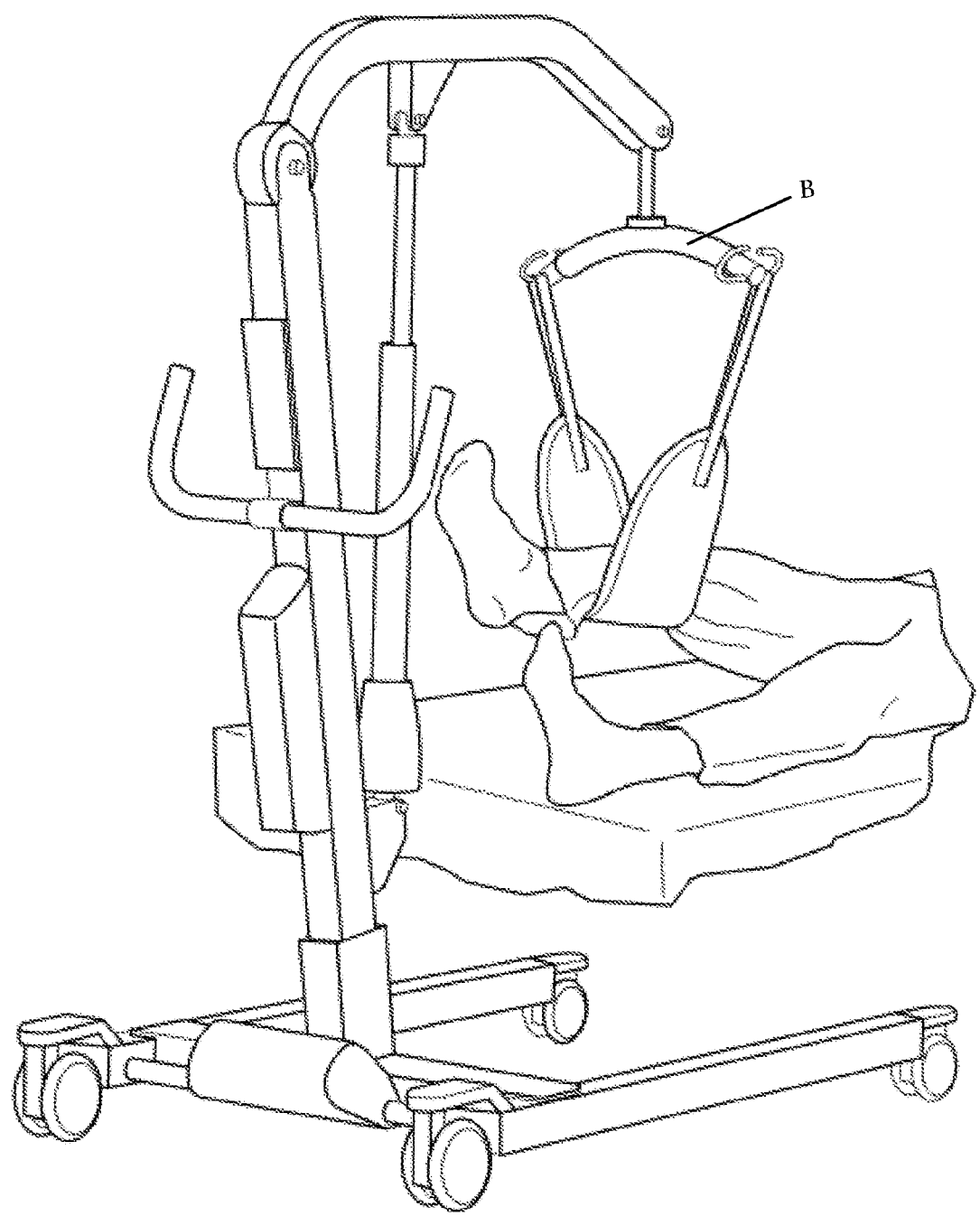
FIG. 33 shows the basic configuration of a prior art lift system having a support framework, cross bar and sling for supporting a patient's body portion.

In additional embodiments, the slings can be fitted with a sterility pouches 200 with interior space 201 as shown in FIGS. 32A and B. The pouches can be polypropylene or polyethylene, opaque or clear. In preferred embodiments the pouch can be RF molded to the top side of the sling running almost the length of the sling. The pouch can be attached by numerous other means as well including stitching, molded by RF into the reinforcement webbing and the like. In further preferred embodiments, the pouch 200 can be self-sealable by adhesive tape 202 band running the length of the pouch opening at 'a' and/or an elastic cord 203 can be incorporated into the lip of the pouch opening to keep the opening held taught or (with adhesive tape) stuck in place. Generally, the elongate pouches can be placed between the belt slots 32 and the edge webbing of the sling. In use, it is common for a sling to be used with only one side of the sling hooked to the crossbar. In this situation, the patient is supported by a table with the unhooked side of the sling draped over the side of the patient table support. Often surgical procedures can cause the sling to become soiled by medical tools and patient tissues and/or become unsterile. To avoid such situations, the elongate pouch on the edge of the sling can be used to store unused sling loops 300 and even the entire length of the unused portion of the sling itself stuffed into or otherwise folded into the pouch. Further, from a manufacturing, sterilizing and preparation by the operation room technician, perspective, the pouches are convenient also in that the sling can be made, packaged, and sterilized with the sling folded in the pouches. With only three steps the sling sides can be stuffed into the pockets (step 1 FIG. 32B), folded over once (step 2), then folded in half lengthwise (step 3) and packaged for sterilization process. In further use, the technician can prep the sling by unfolding each side as needed without disturbing the unused portion of the sling. Further, in an alternate embodiment, the opening of the pouches 'b' can be located on the internal side of the sling as opposed to facing the outer edge of the sling as depicted in FIG. 32C. This embodiment, will also allow for insertion of the sling loops and folding of the sling for sterile packaging.

With respect to specific equipment currently used with patient lifting hoists that can be covered by the sterile drapes of the invention, Table I lists crossbar configurations commonly encountered. The identification data shown in Table I is that of the product manufacturing company, Liko, Inc.

TABLE I

| Universal | Figure | Maximum |
|---|---|---|
| Mini 220 | 11 | 205 kg (450 |
| 350 | 12 | 300 kg (660 |
| 450 | 13 | 300 kg (660 |
| Twin bar | 14 | 300 kg (660 |
| 600 | 15 | 300 kg (660 |
| Cross bar | 16 | 300 kg (660 |
| Universal | 17 | 300 kg (660 |

*= product identifiers are that of Liko company,

Table II lists various models of both floor based and overhead mounted patient lifting hoists that can be covered with the sterile drape systems of the invention. The product identifiers are those of the manufacturer, Liko, Inc.

TABLE II

| Hoist Apparatus | Figure | Maximum |
|---|---|---|
| Floor Based | | |
| Golva ® | 21 | 200 kg (440 |
| Uno100/102 | 22 | 160-205 |
| Uno200 | 23 | 160-205 |
| LikoLight | 24 | 140 kg (308 |
| Viking ® XL | 25 | 300 kg (660 |
| Viking ® L | 26 | 250 kg (550 |
| Viking ® M | 27 | 205 kg (450 |
| Viking ® S | 28 | 160 kg (350 |
| Viking ® XS | 29 | 160 kg (350 |
| Overhead | | |
| Likorall 242 | # | 200-250 kg |
| Likorall 242S | # | 200-250 kg |
| Likorall 243 | # | 200-250 kg |
| Likorall 250 | # | 200-250 kg |
| Likorall R2R | # | 200-250 kg |
| Multirall 200 | # | 200-250 kg |

# = all Overhead systems are similar to the model depicted in FIG. 10.

In table III is listed the average range of body part weights per weight range of a person. This therefore shows how heavy heads, arms and legs can be that are to be supported by a sealed sling.

TABLE III

| Patient Weight lbs | Body Part | Body Part |
|---|---|---|
| 120 lbs (54 kg) | Leg | 19 lbs (9 kg) |
| | Arm | 6 lbs (3 kg) |
| | Head | 10 lbs (5 kg) |
| 120-160 lbs (54-73 kg) | Leg | 25 lbs (11 kg) |
| | Arm | 8 lbs (4 kg) |
| | Head | 13 lbs (6 kg) |
| 160-200 lbs (73-91 kg) | Leg | 31 lbs (14 kg) |
| | Arm | 10 lbs (5 kg) |
| | Head | <17 lbs (8 kg) |
| 200-240 lbs (91-109 kg) | Leg | 38 lbs (17 kg) |
| | Arm | <12 lbs (6 kg) |
| | Head | 20 lbs (9 kg) |
| 240-280 lbs (109-127 | Leg | <44 lbs (20 kg) |
| | Arm | <14 lbs (6 kg) |
| | Head | <24 lbs (11 kg) |
| 280-320 lbs (127-145 | Leg | 50 lbs (23 kg) |
| | Arm | 16 lbs (7 kg) |
| | Head | <27 lbs (12 kg) |
| >360 lbs (>163 kg) | Leg | ?.57 lbs (26 kg) |
| | Arm | ?.18 lbs (8 kg) |
| | Head | ?.30 lbs (14 kg) |

Figure 11A:
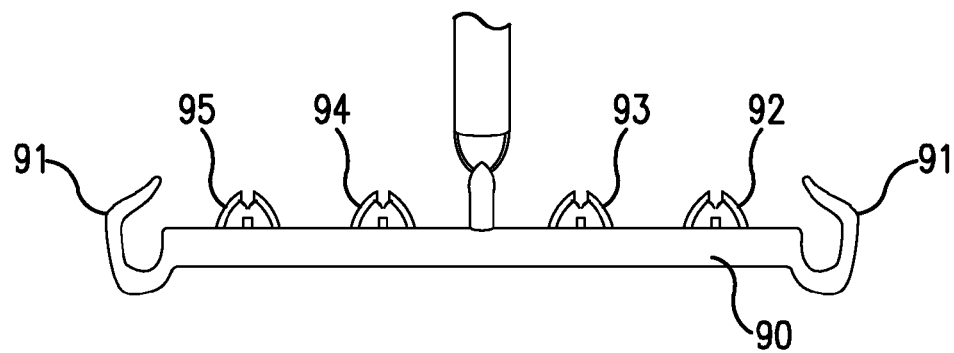
FIGS. 11A, B and C are drawings depicting a novel crossbar 90 of the invention comprising a plurality of sling loop hanging positions. Specifically, in FIG. 11A crossbar 90 is shown with additional sling hooks along the top of the bar.
Figure 11B:
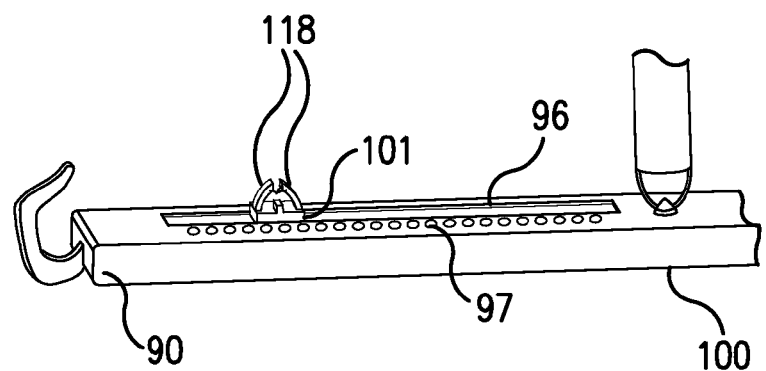
In FIG. 11B is shown an alternate embodiment of the crossbar shown in FIG. 11A which depicts one side of a crossbar 90 to its fulcrum 100 possessing adjustable sling hooks wherein the dual hook points 118 are on a shuttle cock 101 which can slide along slot 96 and is held in place by spring pin 109 which seats into adjustment holes 97.
Figure 11C:
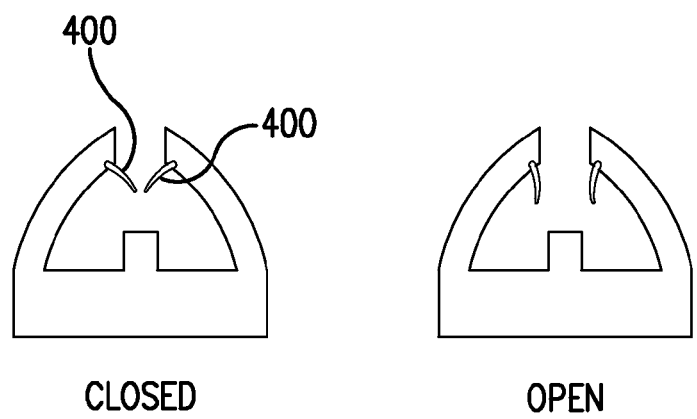
In FIG. 11C the latches 400 can be spring loaded so that when they are pushed to an open position they will automatically spring back to closed position when released.

Given the weight of a typical human body as illuminated in Table III, it can be seen that supporting body weight properly so that each part is not stressed is important. One issue that commonly arises with patient lifting in slings is that the sling loops must be hung on the end crossbar hooks which are a set distance apart. The problem arises when the internal side loops are stretched apart to reach the crossbar end hooks. Hanging the loops from such position causes the sling to warp and fold. Further, when a body is lying in the sling the folds and warps cause highly undesirable pressures on the body and can cause difficulty in manipulating the patient. To overcome such problems, the present invention includes new and improved crossbars that support internal sling loop hooks. Preferably, the crossbar can be constructed from any of high tensile strength steel, aluminum, or composite material capable of supporting at least 200 pounds of force on the bar and hanging hooks. Specifically, as depicted in FIG. 11A, a crossbar 90 is disclosed with at least two, preferably three and even four or more additional bidirectional sling hooks here depicted as hooks 92, 93, 94, and 95 on either side of the hanging belt. In a particularly preferred embodiment there are between two and four internal hook systems each comprising two hooks and a center keeper bar. Crossbars with these features can be manufactured with fixed position internal hooks, or can be manufactured to accommodate an adjustable hook. FIG. 11B a cross bar can be constructed as a hollow tube constructed from high tensile strength steel, aluminum or composite material, as most crossbars are now manufactured, and the top portion thereof can be slotted 96 to accommodate a shuttle cock 101 that is itself a dual crossbar hook 104 with keeper bar 102. The shuttle cock as detailed in FIGS. 12A, B, and C can have a base plate 110 that keeps the shuttle cock from falling out of the slot and further allows the cock to slide along the bar. The cock is kept in a particular position by spring 105 loaded push button 109. To move the cock, the technician can simply push down on the button while the crossbar in inside the drape and slide the cock to the next buttonhole. The cock can be slide to any position needed. Since the bars equipped with such a mechanism also include at least two cocks per side, the bar can effectively position, using the end hooks as well, a sling with at least five to six straps per side. Further in one embodiment, the crossbars and shuttle cocks can be constructed of ³⁄₁₆ to ¼-inch steel or aluminum and the shuttle cock button 109 can be made robust with a high tension spring. In FIG. 11C is depicted slight detail of the hook latches. Here it is contemplated for the latches to be spring loaded so that the sling loops can be fitted over the hooks and the latches can spring back to closed position.

Many different styles of multi-hooked crossbars can be made. FIGS. 30A-D show examples of different bar styles equipped with internal hook systems.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. In combination with a patient hoist system presenting a support framework for a depending cross bar and a sling suspended from the cross bar, the sling supporting a patient body portion, a sterile encapsulation apparatus comprising:
   a drape presenting a flexible body spanning first and second ends;
   an opening at said first drape end adapted to slide over the cross bar in extension away from said second drape end to cover the cross bar and support framework of the hoisting apparatus, said second end of said drape adjacent the cross bar;
   a first reinforcing web at said second end of said drape, said first reinforcing web adjacent the cross bar upon said drape covering the cross bar and support framework of the hoist system;
   a second reinforcing web on the sling for contacting said first reinforcing web of said drape upon the suspension of the support sling from the cross bar, said contact of said first and second reinforcing webs diminishing stresses acting therebetween upon the sling supporting the patient body portion.

2. The apparatus as claimed in claim 1 wherein the sling presents at least one loop at respective ends of the sling, said second reinforcing web along said at least one loop.

3. The apparatus as claimed in claim 1 wherein the support framework of the patient hoist system includes a ground support base, said first end of said drape surrounding the base upon said drape covering the framework and cross bar.

4. The apparatus as claimed in claim 1 wherein the support framework of the patient hoist system depends from an overhead support, said first end of said drape surrounding the depending framework and cross bar.

* * * * *